United States Patent
Wehner et al.

(10) Patent No.: US 12,103,957 B2
(45) Date of Patent: *Oct. 1, 2024

(54) NYESO TCR

(71) Applicant: MEDIGENE IMMUNOTHERAPIES GMBH, Planegg-Martinsried (DE)

(72) Inventors: Carina Wehner, Munich (DE); Manon Weis, Munich (DE)

(73) Assignee: MEDIGENE IMMUNOTHERAPIES GMBH, Planegg-Martinsried (DE)

(*) Notice: Subject to any disclaimer, the term of this patent is extended or adjusted under 35 U.S.C. 154(b) by 293 days.

This patent is subject to a terminal disclaimer.

(21) Appl. No.: 17/588,703

(22) Filed: Jan. 31, 2022

(65) Prior Publication Data
US 2022/0332784 A1    Oct. 20, 2022

Related U.S. Application Data

(63) Continuation of application No. 16/480,987, filed as application No. PCT/EP2019/051963 on Jan. 28, 2019, now Pat. No. 11,267,864.

(30) Foreign Application Priority Data

Feb. 26, 2018   (LU) ........................................ 100715

(51) Int. Cl.
C07K 14/725    (2006.01)
C07K 16/28     (2006.01)

(52) U.S. Cl.
CPC ...... C07K 14/7051 (2013.01); C07K 16/2809 (2013.01)

(58) Field of Classification Search
CPC ............................ A61K 39/46; C07K 14/7051
See application file for complete search history.

(56) References Cited

FOREIGN PATENT DOCUMENTS

| | | |
|---|---|---|
| JP | 2008-509090 A | 3/2008 |
| WO | WO-2005/113595 A2 | 12/2005 |
| WO | WO-2017/044661 A1 | 3/2017 |
| WO | WO-2017/109496 A1 | 6/2017 |
| WO | WO-2017/177337 A1 | 10/2017 |

OTHER PUBLICATIONS

Edes et al. In Vivo Transduction of T Cells: The Future of Immunotherapy .Molecular Therapy vol. 24, Supplement 1, May 2016 (Year: 2016).*
T-cell receptor gene transfer exclusively to human CD8 cells enhances tumor cell killing. Blood, Nov. 22, 2012 vol. 120, No. 22 (Year: 2012).*
International Search Report and Written Opinion for International Application No. PCT/EP2017/051963, mailed Jun. 11, 2019 (16 pages).
Liddy et al., "Monoclonal TCR-redirected tumor cell killing," Nat Med. 18(6):980-7 (2012) (9 pages).
Luxembourg Search Report and Written Opinion for Application No. LU 100715, Le Gouvernement Du Grand-Duche de Luxembourg, completed on May 29, 2018 (11 pages).
McCormack et al., "Bi-specific TCR-anti CD3 redirected T-cell targeting of NY-ESO-1- and LAGE-1-positive tumors," Cancer Immunol Immunother. 62(4):773-85 (2013).
Purbhoo et al., "Quantifying and imaging NY-ESO-1/LAGE-1-derived epitopes on tumor cells using high affinity T cell receptors," J Immunol. 176(12):7308-16 (2006).
Rapoport et al., "NY-ESO-1-specific TCR-engineered T cells mediate sustained antigen-specific antitumor effects in myeloma," Nat Med. 21(8):914-21 (2015).
Rapoport et al., "NY-ESO-1-specific TCR-engineered T cells mediate sustained antigen-specific antitumor effects in myeloma: Supplemental Information," Nat Med. 21(8):914-21 (2015).

* cited by examiner

*Primary Examiner* — Amy E Juedes
*Assistant Examiner* — Brian Hartnett
(74) *Attorney, Agent, or Firm* — Clark & Elbing LLP

(57) ABSTRACT

The present invention relates to an isolated T cell receptor (TCR) specific for NY-ESO-1/LAGE-1 and a polypeptide comprising a functional portion of the TCR. Further implicated are a multivalent TCR complex, a nucleic acid encoding a TCR, a cell expressing the TCR and a pharmaceutical composition comprising the TCR. The invention also refers to the TCR for use as a medicament, in particular to the TCR for use in the treatment of cancer.

20 Claims, 10 Drawing Sheets

Figure 1:
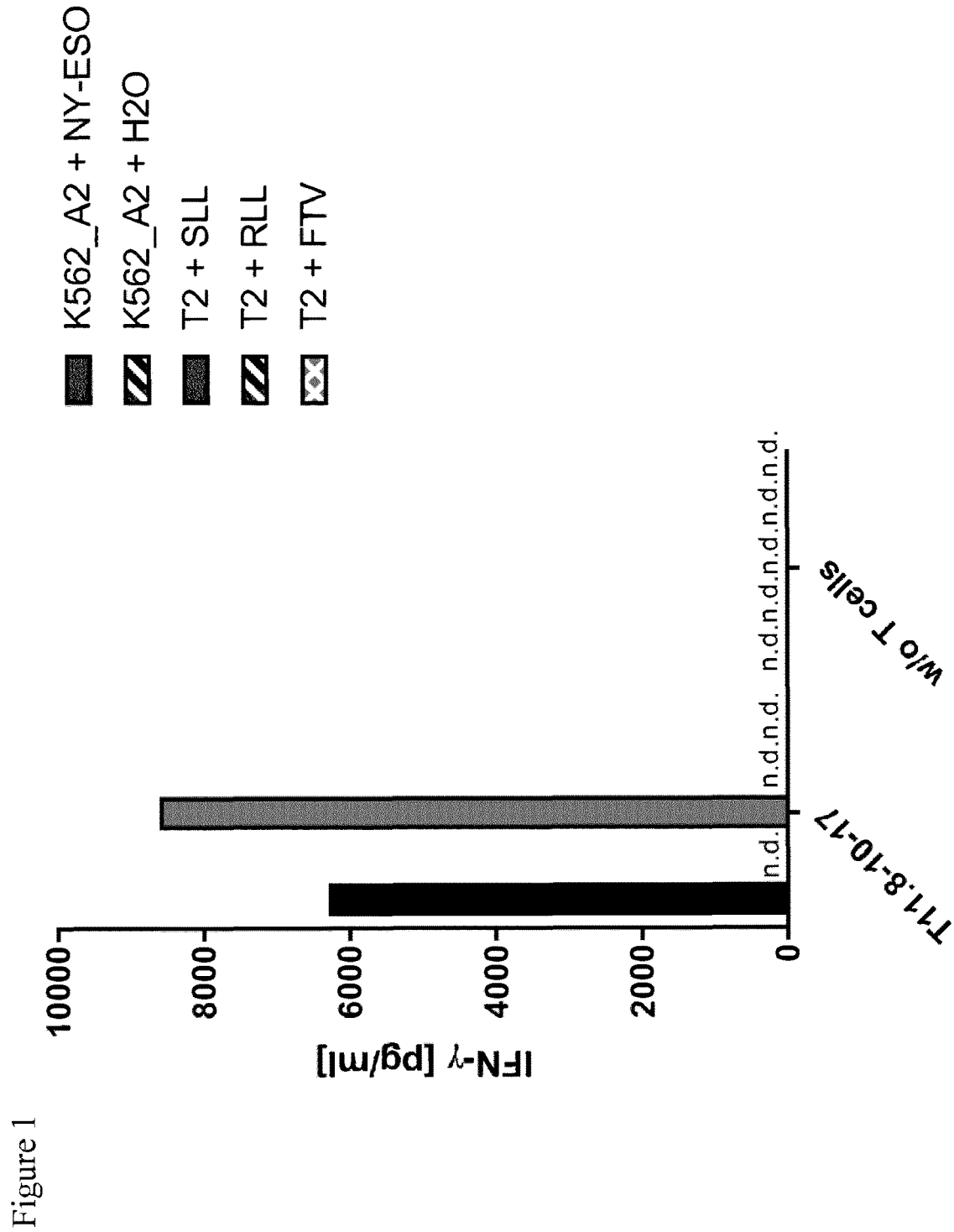

Specification includes a Sequence Listing.

SEQUENCE LISTING

```
<160> NUMBER OF SEQ ID NOS: 22

<210> SEQ ID NO 1
<211> LENGTH: 5
<212> TYPE: PRT
<213> ORGANISM: Homo sapiens

<400> SEQUENCE: 1

Leu Leu Met Trp Ile
1               5

<210> SEQ ID NO 2
<211> LENGTH: 6
<212> TYPE: PRT
<213> ORGANISM: Homo sapiens

<400> SEQUENCE: 2

Ser Leu Leu Met Trp Ile
1               5

<210> SEQ ID NO 3
<211> LENGTH: 9
<212> TYPE: PRT
<213> ORGANISM: Homo sapiens

<400> SEQUENCE: 3

Ser Leu Leu Met Trp Ile Thr Gln Cys
1               5

<210> SEQ ID NO 4
<211> LENGTH: 6
<212> TYPE: PRT
<213> ORGANISM: Homo sapiens

<400> SEQUENCE: 4
```

Asp Arg Gly Ser Gln Ser
1               5

<210> SEQ ID NO 5
<211> LENGTH: 6
<212> TYPE: PRT
<213> ORGANISM: Homo sapiens

<400> SEQUENCE: 5

Ile Tyr Ser Asn Gly Asp
1               5

<210> SEQ ID NO 6
<211> LENGTH: 9
<212> TYPE: PRT
<213> ORGANISM: Homo sapiens

<400> SEQUENCE: 6

Cys Ala Ala Asp Asp Lys Ile Ile Phe
1               5

<210> SEQ ID NO 7
<211> LENGTH: 5
<212> TYPE: PRT
<213> ORGANISM: Homo sapiens

<400> SEQUENCE: 7

Ser Gly His Asp Tyr
1               5

<210> SEQ ID NO 8
<211> LENGTH: 6
<212> TYPE: PRT
<213> ORGANISM: Homo sapiens

<400> SEQUENCE: 8

Phe Asn Asn Asn Val Pro
1               5

<210> SEQ ID NO 9
<211> LENGTH: 10
<212> TYPE: PRT
<213> ORGANISM: Homo sapiens

<400> SEQUENCE: 9

Cys Ala Ser Ser Arg Gly Gly Ser Gly Tyr
1               5                   10

<210> SEQ ID NO 10
<211> LENGTH: 129
<212> TYPE: PRT
<213> ORGANISM: Homo sapiens

<400> SEQUENCE: 10

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

```
Pro Glu Leu Ile Met Phe Ile Tyr Ser Asn Gly Asp Lys Glu Asp Gly
 65                  70                  75                  80

Arg Phe Thr Ala Gln Leu Asn Lys Ala Ser Gln Tyr Val Ser Leu Leu
                 85                  90                  95

Ile Arg Asp Ser Gln Pro Ser Asp Ser Ala Thr Tyr Leu Cys Ala Ala
            100                 105                 110

Asp Asp Lys Ile Ile Phe Gly Lys Gly Thr Arg Leu His Ile Leu Pro
            115                 120                 125

Asn
```

<210> SEQ ID NO 11
<211> LENGTH: 132
<212> TYPE: PRT
<213> ORGANISM: Homo sapiens

<400> SEQUENCE: 11

```
Met Gly Ser Trp Thr Leu Cys Cys Val Ser Leu Cys Ile Leu Val Ala
  1               5                  10                  15

Lys His Thr Asp Ala Gly Val Ile Gln Ser Pro Arg His Glu Val Thr
                 20                  25                  30

Glu Met Gly Gln Glu Val Thr Leu Arg Cys Lys Pro Ile Ser Gly His
             35                  40                  45

Asp Tyr Leu Phe Trp Tyr Arg Gln Thr Met Met Arg Gly Leu Glu Leu
         50                  55                  60

Leu Ile Tyr Phe Asn Asn Asn Val Pro Ile Asp Asp Ser Gly Met Pro
 65                  70                  75                  80

Glu Asp Arg Phe Ser Ala Lys Met Pro Asn Ala Ser Phe Ser Thr Leu
                 85                  90                  95

Lys Ile Gln Pro Ser Glu Pro Arg Asp Ser Ala Val Tyr Phe Cys Ala
            100                 105                 110

Ser Ser Arg Gly Gly Ser Gly Tyr Thr Phe Gly Ser Gly Thr Arg Leu
            115                 120                 125

Thr Val Val Glu
            130
```

<210> SEQ ID NO 12
<211> LENGTH: 269
<212> TYPE: PRT
<213> ORGANISM: Homo sapiens

<400> SEQUENCE: 12

```
Met Lys Ser Leu Arg Val Leu Leu Val Ile Leu Trp Leu Gln Leu Ser
  1               5                  10                  15

Trp Val Trp Ser Gln Gln Lys Glu Val Glu Gln Asn Ser Gly Pro Leu
                 20                  25                  30

Ser Val Pro Glu Gly Ala Ile Ala Ser Leu Asn Cys Thr Tyr Ser Asp
             35                  40                  45

Arg Gly Ser Gln Ser Phe Phe Trp Tyr Arg Gln Tyr Ser Gly Lys Ser
         50                  55                  60

Pro Glu Leu Ile Met Phe Ile Tyr Ser Asn Gly Asp Lys Glu Asp Gly
 65                  70                  75                  80

Arg Phe Thr Ala Gln Leu Asn Lys Ala Ser Gln Tyr Val Ser Leu Leu
                 85                  90                  95

Ile Arg Asp Ser Gln Pro Ser Asp Ser Ala Thr Tyr Leu Cys Ala Ala
            100                 105                 110

Asp Asp Lys Ile Ile Phe Gly Lys Gly Thr Arg Leu His Ile Leu Pro
```

```
                    115                 120                 125
Asn Ile Gln Asn Pro Asp Pro Ala Val Tyr Gln Leu Arg Asp Ser Lys
    130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Thr
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
        195                 200                 205

Ile Ile Pro Glu Asp Thr Phe Phe Pro Ser Ser Asp Val Pro Cys Asp
    210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 13
<211> LENGTH: 308
<212> TYPE: PRT
<213> ORGANISM: Homo sapiens

<400> SEQUENCE: 13

Met Gly Ser Trp Thr Leu Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asp Tyr Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Arg Gly Gly Ser Gly Tyr Thr Phe Gly Ser Gly Thr Arg Leu
        115                 120                 125

Thr Val Val Glu Asp Leu Asn Lys Val Phe Pro Pro Glu Val Ala Val
    130                 135                 140

Phe Glu Pro Ser Lys Ala Glu Ile Ala His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220
```

```
Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
            245                 250                 255

Trp Gly Arg Ala Asp Cys Gly Ile Thr Ser Ala Ser Tyr His Gln Gly
        260                 265                 270

Val Leu Ser Ala Thr Ile Leu Tyr Glu Ile Leu Leu Gly Lys Ala Thr
    275                 280                 285

Leu Tyr Ala Val Leu Val Ser Ala Leu Val Leu Met Ala Met Val Lys
    290                 295                 300

Arg Lys Asp Phe
305

<210> SEQ ID NO 14
<211> LENGTH: 180
<212> TYPE: PRT
<213> ORGANISM: Homo sapiens

<400> SEQUENCE: 14

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 15
<211> LENGTH: 10
<212> TYPE: PRT
<213> ORGANISM: Homo sapiens

<400> SEQUENCE: 15

Phe Thr Val Ser Gly Asn Ile Leu Thr Ile
1               5                   10

<210> SEQ ID NO 16
<211> LENGTH: 9
<212> TYPE: PRT
<213> ORGANISM: Homo sapiens
```

```
<400> SEQUENCE: 16

Arg Leu Leu Glu Phe Tyr Leu Ala Met
1               5

<210> SEQ ID NO 17
<211> LENGTH: 9
<212> TYPE: PRT
<213> ORGANISM: Homo sapiens

<400> SEQUENCE: 17

Ile Cys Leu Gln Trp Ile Thr Gln Cys
1               5

<210> SEQ ID NO 18
<211> LENGTH: 9
<212> TYPE: PRT
<213> ORGANISM: Homo sapiens

<400> SEQUENCE: 18

Ser Leu Leu Phe Trp Ile Leu Ile Cys
1               5

<210> SEQ ID NO 19
<211> LENGTH: 9
<212> TYPE: PRT
<213> ORGANISM: Homo sapiens

<400> SEQUENCE: 19

Ser Leu Leu Met Trp Met Leu Arg Leu
1               5

<210> SEQ ID NO 20
<211> LENGTH: 9
<212> TYPE: PRT
<213> ORGANISM: Homo sapiens

<400> SEQUENCE: 20

Asn Leu Leu Phe Trp Ile Cys Gly Cys
1               5

<210> SEQ ID NO 21
<211> LENGTH: 9
<212> TYPE: PRT
<213> ORGANISM: Homo sapiens

<400> SEQUENCE: 21

Ser Leu Met Tyr Trp Ile Thr Ile Gln
1               5

<210> SEQ ID NO 22
<211> LENGTH: 9
<212> TYPE: PRT
<213> ORGANISM: Homo sapiens

<400> SEQUENCE: 22

Gln Leu Leu Gly Trp Ile Thr Ala His
1               5
```

NYESO TCR

SEQUENCE LISTING

The instant application contains a Sequence Listing which has been submitted electronically in ASCII format and is hereby incorporated by reference in its entirety. Said ASCII copy, created on Jan. 28, 2022, is named 50796-034002_Sequence_Listing_1_28_22_ST25 and is 11,714 bytes in size.

FIELD OF THE INVENTION

The present invention relates to an isolated T cell receptor (TCR) specific for NY-ESO-1/LAGE-1 and polypeptide comprising a functional portion of the TCR. Further implicated are a multivalent TCR complex, a nucleic acid encoding a TCR, a cell expressing the TCR and a pharmaceutical composition comprising the TCR. The invention also refers to the TCR for use as a medicament, in particular to the TCR for use in the treatment of cancer.

BACKGROUND OF THE INVENTION

T lymphocytes (or T cells) which form part of the cell-mediated immune system play a major role in the eradication of pathogens. T cells develop in the thymus and express T cell receptor molecules on their surface that allow the recognition of peptides presented on major histocompatibility complex (MHC) molecules which are expressed on nucleated cells (known as antigen presentation). Antigens derived from pathogens, i.e. foreign antigens presented by MHC molecules will elicit a powerful T cell response whereas self-antigens usually do not lead to a T cell response due to a negative selection of self-antigen specific T cells in the thymus during the development of such T cells. The immune system can thus discriminate between nucleated cells presenting foreign- or self-antigens and specifically target and eradicate infected cells via potent cytokine release and cellular cytotoxicity mechanisms of the T cells.

The power of the immune system has been recognized as a promising tool for future cancer therapies. In the last decade, research has begun to exploit the unique properties of T cells by using adoptive cell transfer (ACT), which involves the administration of patient-derived lymphocytes, expanded ex vivo. ACT is an attractive concept for the treatment of cancer because it does not require immune-competence of patients, and the specificity of transferred lymphocytes can be targeted against non-mutated and thus poorly immunogenic tumor antigens that typically fail to effectively trigger autologous T cell responses. Although ACT has been shown to be a promising treatment for various types of cancer, its broad application as clinical treatment has been hampered by the need for custom isolation and characterization of tumor-specific T cells from each patient—a process that can be not only difficult and time-consuming but also often fails to yield high-avidity T cells (Xue et al. Clin. Exp. Immunol. 2005 February; 139(2): 167-172; Schmitt et al., Hum. Gene Ther. 2009 November; 20(11): 1240-1248.)

The genetic transfer of tumor antigen-specific T-cell receptors (TCRs) into primary T cells can overcome some of the current limitations of ACT, as it allows for the rapid generation of tumor-reactive T lymphocytes with defined antigen specificity even in immunocompromised patients. However, the identification of suitable T cell clones bearing TCRs that specifically recognize tumor antigens and exhibit the desired anti-tumor effects in vivo is still the topic of ongoing research. Considering that in 2012 about 14.1 million new cases of cancer occurred globally and that cancer currently is the cause of about 14.6% of all human deaths worldwide, novel and efficient treatment options are urgently needed. It is the object of the present invention to comply with the needs set out above.

NY-ESO-1 and LAGE-1 are important immunotherapeutic target antigens belonging to the family of Cancer/Testis antigens. Cancer/Testis antigens are expressed in various malignant tumors and germ cells of the testis but not on other adult tissues.

Hence, it is particularly desirable to provide TCRs or derivatives thereof specific for NY-ESO-1/LAGE-1.

OBJECTIVES AND SUMMARY OF THE INVENTION

To meet these needs, it is an objective of the invention to provide an isolated T cell receptor (TCR) specific for NY-ESO-1/LAGE-1. In particular, the TCR specifically recognizes the amino acid sequence SEQ ID NO: 1 or a fragment thereof. More particularly, the TCR specifically recognizes the amino acid sequence SEQ ID NO: 2 or a fragment thereof. Even more particularly, the TCR specifically recognizes the amino acid sequence SEQ ID NO: 3 or a fragment thereof.

In particular, the TCR of the invention recognizes the antigenic target NY-ESO-1/LAGE-1 when being presented on an MHC molecule of a target cell, specifically an MHC-I molecule, and in particular an HLA-A molecule, preferably HLA-A*02 and specifically HLA-A2 molecules encoded by the allele HLA-A*02:01 (the T cell or TCR is said to be "restricted" to a particular MHC molecule). It is also conceivable that the TCR of the invention recognizes the antigenic target presented on other HLA-A*02 alleles.

In a specific embodiment, the TCR recognizes the HLA-A*02 bound form of the amino acid sequence of SEQ ID NO: 1, SEQ ID NO: 2 and/or SEQ ID NO: 3. In specific embodiments, the TCR specifically recognizes the HLA-A*02:01 bound form of the amino acid sequence of SEQ ID NO: 1, SEQ ID NO: 2 and/or SEQ ID NO: 3. This TCR is highly specific for NY-ESO and exhibits low cross-reactivity to other peptides.

The invention particularly refers to a TCR having a TCR α chain comprising a complementarity-determining region 3 (CDR3), wherein the CDR3 comprises the sequence of SEQ ID NO: 6. The TCR may have a TCR β chain comprising a CDR3, wherein the CDR3 comprises the amino acid sequence of SEQ ID NO: 9.

More specifically, the TCR according to the invention may comprise
- a TCR α chain comprising a CDR1 having the amino acid sequence of SEQ ID NO: 4, a CDR 2 having the amino acid sequence of SEQ ID NO: 5 and a CDR 3 having the sequence of SEQ ID NO: 6; and
- a TCR β chain comprising a CDR1 having the amino acid sequence of SEQ ID NO: 7, a CDR 2 having the amino acid sequence of SEQ ID NO: 8 and a CDR 3 having the sequence of SEQ ID NO: 9.

Even more specifically, the invention relates to an isolated TCR comprising a variable TCR α region having an amino acid sequence which is at least 80% identical to SEQ ID NO: 10 and a variable TCR β region having an amino acid sequence which is at least 80% identical to SEQ ID NO: 11. In particular, the TCR may comprise a variable TCR α region having the amino acid sequence of SEQ ID NO: 10 and a variable TCR β region having the amino acid sequence of SEQ ID NO: 11.

The isolated TCR may comprise a TCR α chain having an amino acid sequence which is at least 80% identical to SEQ ID NO: 12 and a TCR β chain having an amino acid sequence which is at least 80% identical to SEQ ID NO: 13. More specifically, the isolated TCR may comprise a TCR α chain having the amino acid sequence of SEQ ID NO: 12 and a TCR β chain having the amino acid sequence of SEQ ID NO: 13.

Accordingly, the TCR may comprise a TCR α chain and a TCR β chain, wherein
- the variable TCR α region has an amino acid sequence which is at least 80% identical to SEQ ID NO: 10 and comprises a CDR3 region having the amino acid sequence set out in SEQ ID NO: 6;
- the variable TCR β region has an amino acid sequence which is at least 80% identical to SEQ ID NO: 11 and comprises a CDR3 region having the amino acid sequence set out SEQ ID NO: 9.

The TCR according to the invention is isolated and/or purified and may be soluble or membrane bound.

In some embodiments, the amino acid sequence of the TCR may comprise one or more phenotypically silent substitutions. In addition, the TCRs of the invention can be labelled. Useful labels are known in the art and can be coupled to the TCR or TCR variant using routine methods, optionally via linkers of various lengths. The term "label" or "labelling group" refers to any detectable label. Additionally, or alternatively, the amino acid sequence may be modified to comprise a therapeutic agent or pharmacokinetic modifying moiety. The therapeutic agent may be selected from the group consisting of an immune effector molecule, a cytotoxic agent and a radionuclide. The immune effector molecule may for example be a cytokine. The pharmacokinetic modifying moiety may be at least one polyethylene glycol repeating unit, at least one glycol group, at least one sialyl group or a combination thereof. The TCR, in particular a soluble form of the TCR according to the invention can be modified by attaching additional functional moieties, e.g. for reducing immunogenicity, increasing hydrodynamic size (size in solution) solubility and/or stability (e.g. by enhanced protection to proteolytic degradation) and/or extending serum half-life. Other useful functional moieties and modifications include "suicide" or "safety switches" that can be used to shut off or turn on effector host cells carrying an inventive TCR in a patient's body.

TCRs with an altered glycosylation pattern are also envisaged herein.

It is also conceivable to add a drug or a therapeutic entity, such as a small molecule compound to the TCR, in particular to a soluble form of the inventive TCR.

The TCR, in particular a soluble form of the inventive TCR can additionally be modified to introduce additional domains which aid in identification, tracking, purification and/or isolation of the respective molecule (tags).

In some embodiments, the TCR is of the single chain type, wherein the TCR α chain and the TCR β chain are linked by a linker sequence.

Another aspect of the invention refers to a polypeptide comprising a functional portion of the TCR as described herein, wherein the functional portion comprises one of the amino acid sequences of SEQ ID NOs: 6 and 9.

In specific embodiments, the functional portion comprises the TCR α variable chain and/or the TCR β variable chain.

Specific embodiments refer to a multivalent TCR complex comprising a least two TCRs as described herein. In a more specific embodiment, at least one of said TCRs is associated with a therapeutic agent.

Some embodiments refer to the inventive TCR expressed on an effector cell, especially on an immune effector cell as a functional polypeptide or functional multivalent polypeptide, wherein IFN-γ secretion is induced in the aforementioned effector cell expressing the TCR upon binding to an HLA-A*02 bound form of the amino acid sequence selected from the group consisting of SEQ ID NOs: 1 to 3.

The IFN-γ secretion induced upon binding of the inventive TCR expressed on an effector cell to an HLA-A*02 bound form of the amino acid sequence selected from the group consisting of SEQ ID NOs: 1 to 3 may be more than 3 ng/ml, such as more than 4 ng/ml, more than 5 ng/ml, more preferably more than 6 ng/ml, most preferably even more than 7 ng/ml. The IFN-γ secretion may be at least 4 times higher when binding to an HLA-A*02 bound form of the amino acid sequence selected from the group consisting of SEQ ID NOs: 1 to 3 compared to binding to an HLA-A*02 bound form of an irrelevant peptide (e.g. SEQ ID No: 15 or 16).

Some embodiments refer to the isolated TCR, polypeptide or multivalent TCR complex according to the invention, wherein MIP-1α and MIP-1β secretion induced by binding of the inventive TCR expressed on an effector cell to the HLA-A*02 bound form of the amino acid sequence selected from the group consisting of SEQ ID NOs: 1 to 3 is below a predefined threshold.

The MIP-1α secretion induced by binding of the inventive TCR expressed on an effector cell to the HLA-A*02 bound form of amino acid sequence selected from the group consisting of SEQ ID NOs: 1 to 3 may be less than 1 ng/ml, preferably less than 0.8 ng/ml, more preferably less than 0.7 ng/ml.

The MIP-1β secretion induced by binding of the inventive TCR expressed on an effector cell to the HLA-A*02 bound form of amino acid sequence selected from the group consisting of SEQ ID NOs: 1 to 3 may be less than 3 ng/ml, preferably less than 2.8 ng/ml, more preferably less than 2.5 ng/ml.

Low MIP-1α and MIP-1β secretion levels are advantageous, since chemokines such as MIP-1a and MIP-1β, also named CLL3 and CLL4 respectively, in particular MIP-1α, are known to promote tumor progression (Liao et al. Oncotarget, 7(4): 4310-4325 (2015); Silva et al. Oncotarget 8 (11): 51024-51036 (2017)).

The cytokine and chemokine release, such as IFN-γ secretion and MIP-1α and MIP-1β secretion may be measured using T cell antibody immobilized magnetic beads by an in vitro assay in which T2 cells (Greiner et al. 2006, Blood. 2006 December 15; 108(13):4109-17) transfected with ivtRNA coding one of the amino acid sequences selected from the group consisting of SEQ ID NOs: 1 to 3, preferably SEQ ID NO: 3, are incubated with CD8+ enriched and/or non-CD8+-enriched PBMC expressing the TCR to be investigated or in an in vitro assay using T2 cells loaded with either the NY-ESO-1/LAGE-1$_{157-165}$ (SLL) peptide (SEQ ID NO: 3) or an irrelevant peptide derived from NY-ESO-1 (e.g. SEQ ID NOs: 15 or 16).

Another aspect of the invention refers to a nucleic acid encoding a TCR as described herein or encoding the polypeptide as described above.

A further aspect of the invention refers to a plasmid or vector comprising the nucleic acid of the present application as described above. Preferably, the vector is an expression vector or a vector suitable for the transduction or transfection of cells, especially eukaryotic cells. The vector may be for example a retroviral vector, for example a gamma-retroviral or lentiviral vector.

Another aspect of the invention refers to a cell expressing the TCR as described herein. The cell may be isolated or non-naturally occurring.

Another aspect of the invention refers to a cell comprising the nucleic acid as described above or the plasmid or vector as described above. More specifically, the cell may comprise:
a) an expression vector which comprises at least one nucleic acid as described above, or
b) a first expression vector which comprises a nucleic acid encoding the alpha chain of the TCR as described herein, and a second expression vector which comprises a nucleic acid encoding the beta chain of a TCR as described herein.

The cell may be a peripheral blood lymphocyte (PBL) or a peripheral blood mononuclear cell (PBMC). Typically, the cell is an immune effector cell, especially a T cell. Other suitable cell types include gamma-delta T cells and NK-like T cells.

Another aspect refers to an antibody or antigen binding fragment thereof specifically binding to a portion of the TCR as described herein which mediates specificity for NY-ESO-1/LAGE-1. In a specific embodiment, the portion of the TCR that mediates the NY-ESO-1/Lage-1 specificity comprises the CDR3 of the alpha chain of SEQ ID NO: 6 and/or the CDR3 of the beta chain of SEQ ID NO: 9.

Another aspect of the invention refers to a pharmaceutical composition comprising the TCR as described herein, the polypeptide as described herein, the multivalent TCR complex as described herein, the nucleic acid as described herein, the vector as described herein, the cell as described herein, or the antibody as described herein.

Typically, the pharmaceutical composition comprises at least one pharmaceutically acceptable carrier.

Another aspect of the invention refers to TCR as described herein, the polypeptide as described herein, the multivalent TCR complex as described herein, the nucleic acid as described herein, the vector as described herein, the cell as described herein, or the antibody as described herein for use as a medicament, in particular for use in the treatment of cancer. The cancer may be a hematological cancer or a solid tumor. The cancer may be selected from the group consisting of sarcoma, prostate cancer, uterine cancer, thyroid cancer, testicular cancer, renal cancer, pancreatic cancer, ovarian cancer, esophageal cancer, non-small-cell lung cancer, non-Hodgkin's lymphoma, multiple myeloma, melanoma, hepatocellular carcinoma, head and neck cancer, gastric cancer, endometrial cancer, colorectal cancer, cholangiocarcinoma, breast cancer, bladder cancer, myeloid leukemia and acute lymphoblastic leukemia. Preferably, the cancer is sarcoma or osteosarcoma.

FIGURE LEGENDS

FIG. 1 shows IFN-γ secretion of NY-ESO-$1_{157-165}$-specific T cell clone T11.8-10-17 upon stimulation with either CTAG1B-ivtRNA transfected tumor cell line K562-A2 (stable HLA-A*02:01-transduced K562 cell line, K562 A2+NY-ESO), wherein CTAG1B designates the human gene copy of NY-ESO-1 (CTAG1B-001, Gene ID ENST0000359887), or T2 cells loaded with $10^{-5}$ M NY-ESO-$1_{157-165}$ peptide (T2+SLL), K562-A2 electroporated with water (K562_A2+H2O) or T2 cells loaded with $10^{-5}$ M NY-ESO-1 derived peptides (RLLEFYLAM: T2+RLL and FTVSGNILTI: T2+FTV) were used as negative controls. IFN-γ release [pg/ml] was detected by using standard ELISA.

Figure 2A:
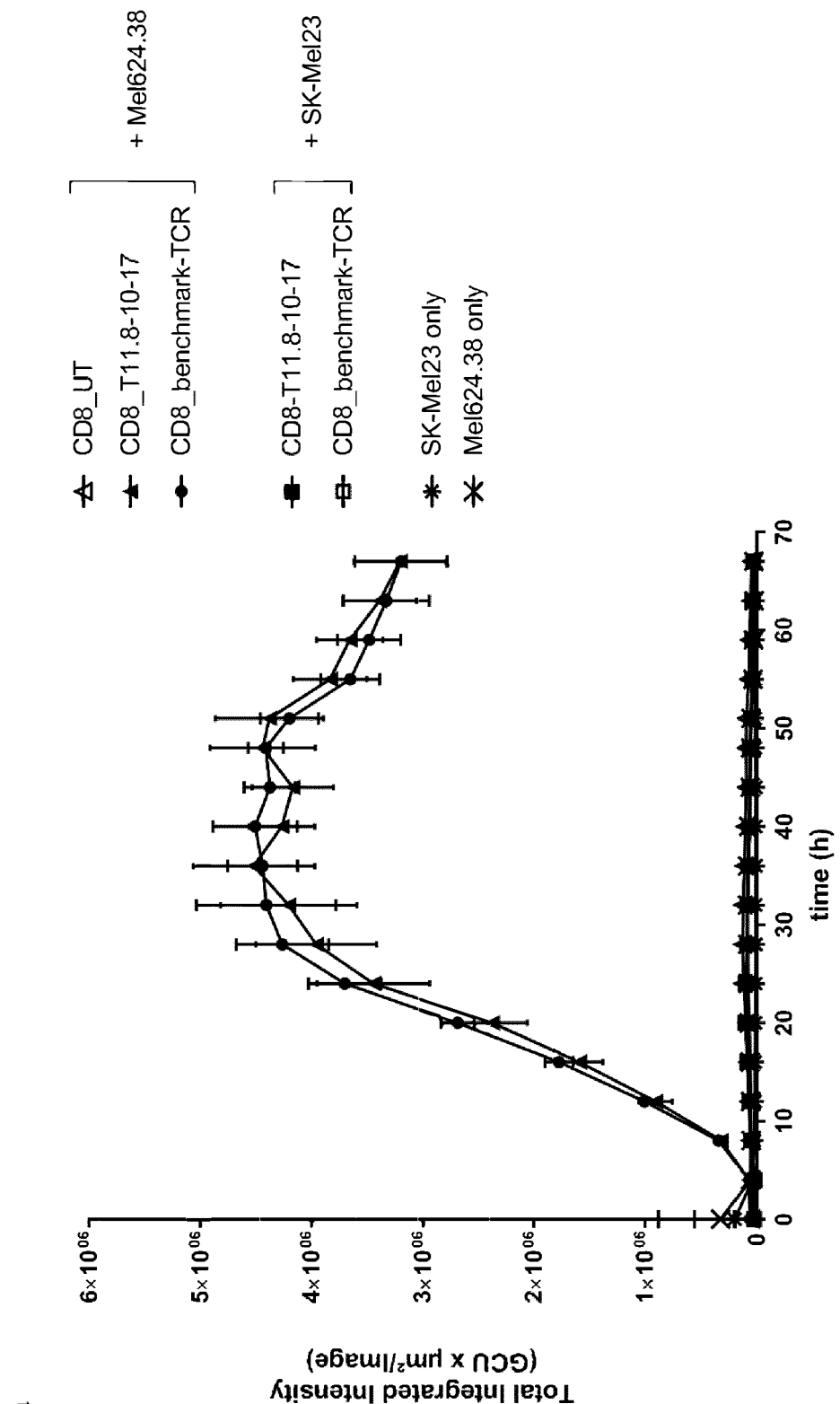
Figure 2B:
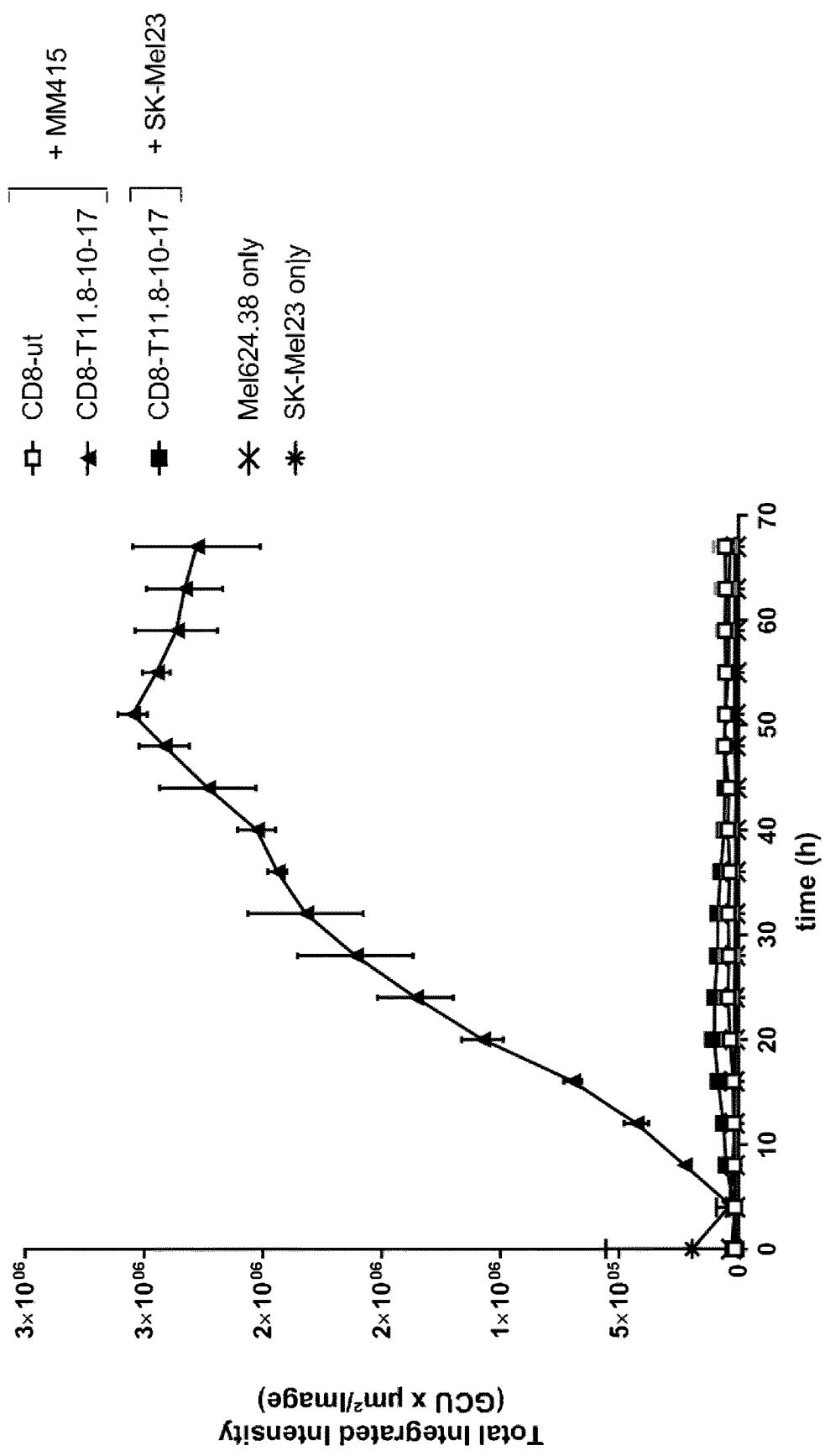

FIGS. 2a and 2b shows killing of HLA-A*02 positive NY-ESO-1/LAGE-1 positive tumor cell lines Me1624.38 (FIG. 2a) and MM415 (FIG. 2b) by CD8$^+$ enriched PBMC expressing the NY-ESO-1/LAGE-$1_{157-165}$-specific TCR T11.8-10-17 (CD8-T11.8-10-17) in comparison to benchmark-TCR transduced T cells (CD8 benchmark-TCR) (FIG. 2a). As a negative control, untransduced CD8$^+$ enriched PBMC were used as effector cells (CD8 UT) or the HLA-A*02 positive, NY-ESO-1/LAGE-1 negative tumor cell line SK-Mel23 was used as a target cell line. An increase of red fluorescent target cells (Total Integrated Intensitiy in GCU× μm$^2$/Image), that indicates induction of apoptosis of target cells (Annexin V, red), was tested every four hours over a total time period of 67 hours by live-cell imaging (IncuCyte® ZOOM).

Figure 3:
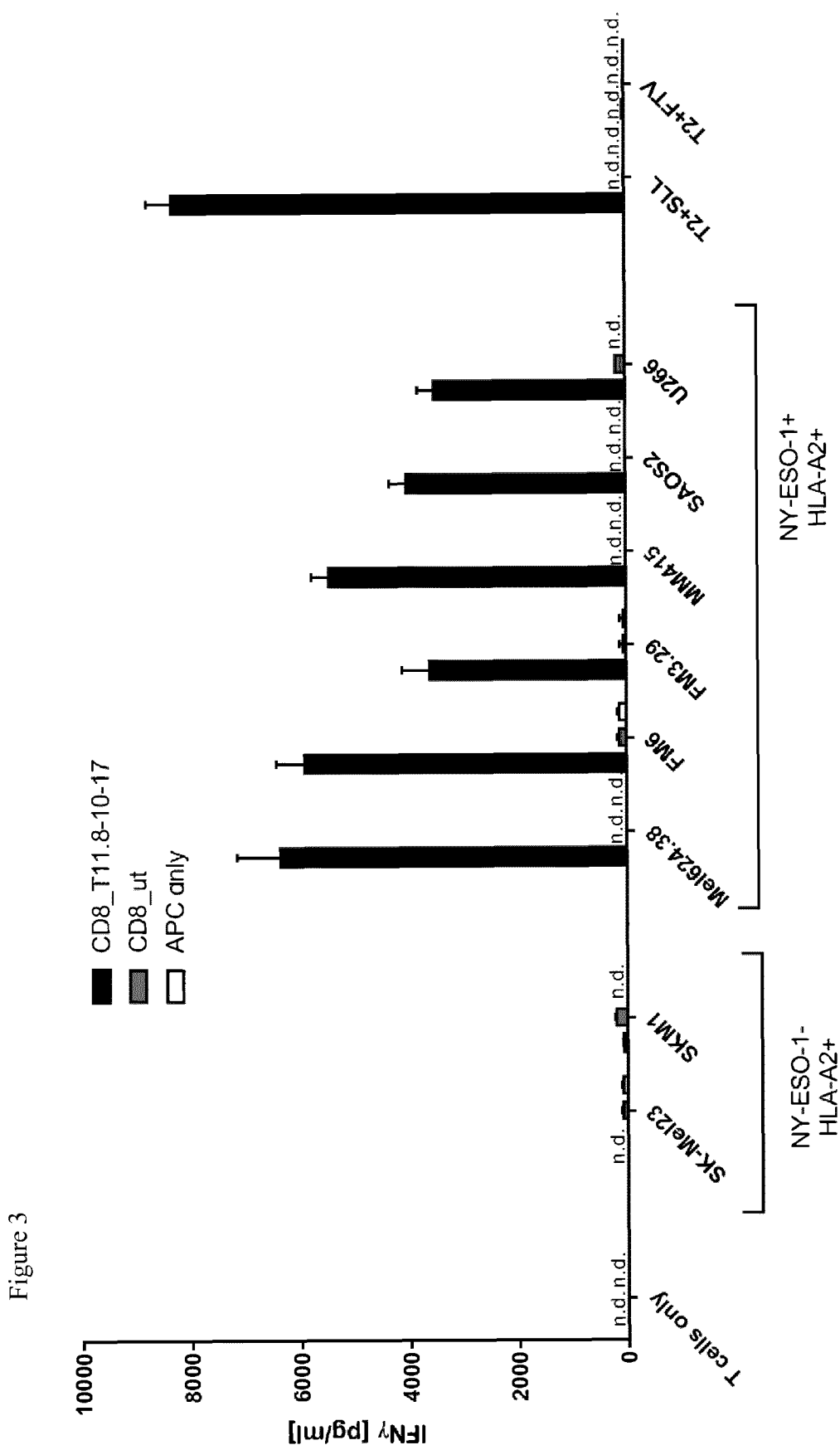

FIG. 3 shows specific IFN-γ release of NY-ESO-1/LAGE-$1_{157-165}$-specific CD8$^+$ enriched PBMC expressing the NY-ESO-1/LAGE-$1_{157-165}$-specific TCR T11.8-10-17 (CD8_T11.8-10-17) in co-culture with either HLA-A*02:01 positive tumor cells that expressed NY-ESO-1/LAGE-1 (Me1624.38, FM6, FM3.29, MM415, SAOS2, U266) or with NY-ESO-1/LAGE-$1_{157-165}$-peptide loaded T2 cells (T2+SLL). Untransduced CD8$^+$ T cells (CD8_ut) do not show IFN-γ release upon co-culture with any tumor cell line or T2 cells. As a negative control, T11.8-10-17 transgenic CD8$^+$ T cells (CD8_T11.8-10-17) or untransduced CD8$^+$ T cells (CD8_ut) co-cultured with either HLA-A*02:01 positive tumor cells that were negative for NY-ESO-1/LAGE-1 mRNA (SK-Mel23, SKM1) or with FTVSGNILTI (irrelevant peptide)-loaded T2 cells (T2+FTV) which show no IFN-γ release. As a further control IFN-γ secretion was tested for antigen presenting cells (APC) cultured without effector T cells. Activation of T11.8-10-17 transgenic CD8$^+$ T cells was measured by using standard ELISA measuring IFN-γ release in [pg/ml].

Figure 4:
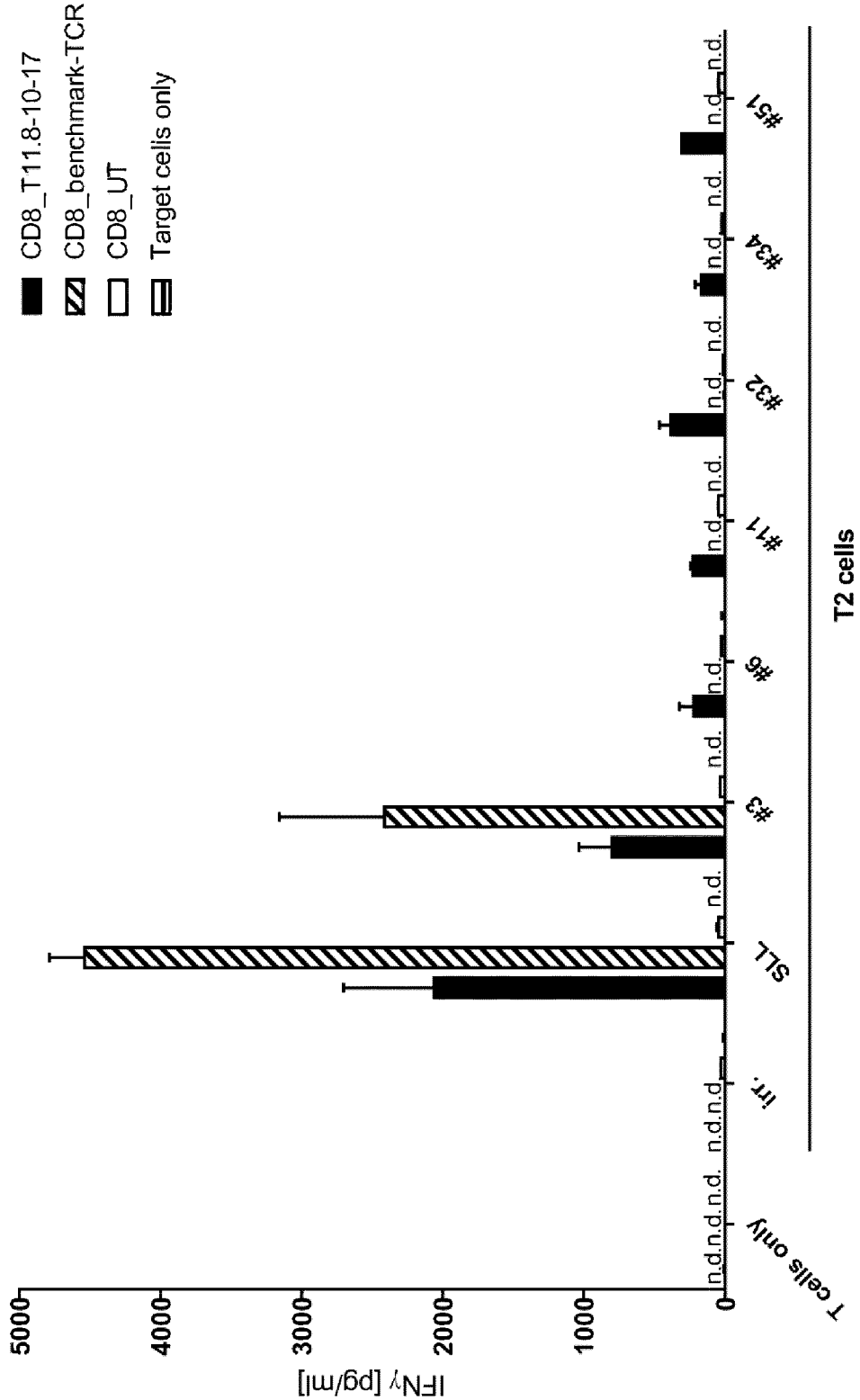

FIG. 4 shows IFN-γ secretion of either NY-ESO-$1_{157-165}$-specific benchmark- or T11.8-10-17-TCR-transduced CD8$^+$ T cells upon stimulation with peptide-loaded ($10^{-5}$ M) T2 cells. Tested peptides were identified by an in silico Expitope® search analysis for peptides (cf. Table 1) that are at least 56% homologous (up to 4 mismatches) to the SLL-peptide sequence. As a negative control, untransduced CD8$^+$ enriched PBMC were used as effector cells or TCR-transgenic T cells were stimulated with irrelevant (irr.; FTVSGNILTI) peptide-loaded T2 cells. As a positive control T cells were activated by SLL peptide-loaded T2 cells. IFN-γ secretion was measured by standard ELISA.

Figure 5:
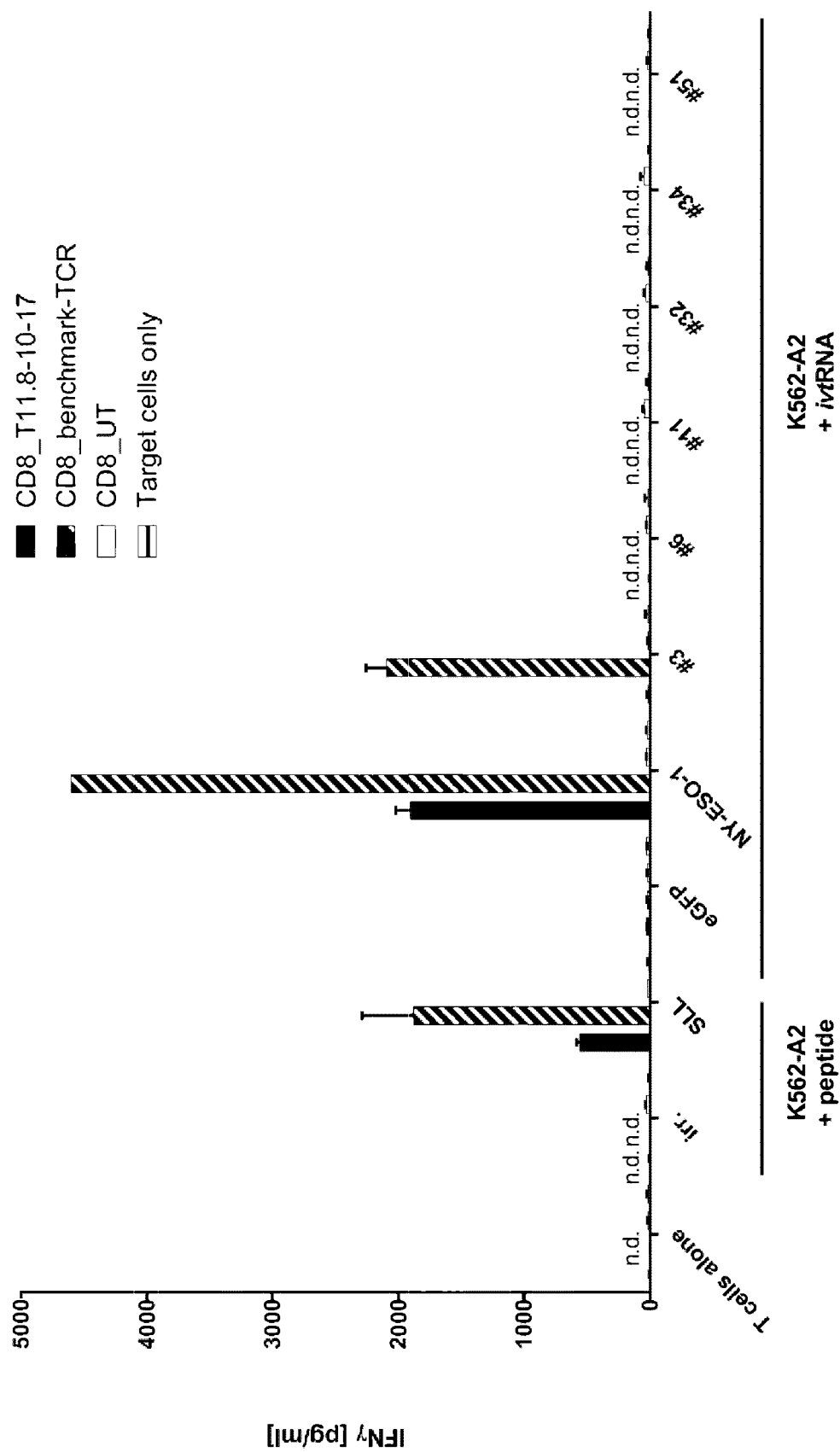

FIG. 5 shows specific IFN-γ release of CD8$^+$ enriched PBMC expressing the NY-ESO-1/LAGE-$1_{157-165}$-specific TCR T11.8-10-17 (CD8_T11.8-10-17) or the NY-ESO-1/LAGE-$1_{157-165}$-specific benchmark-TCR (CD8 benchmark-TCR) in co-culture with either peptide-loaded HLA-A*02:01-transgenic K562 cells (K562-A2+irr, K562-A2+SLL) or with target-ivtRNA transfected HLA-A*02:01-transgenic K562-A2 (K562-A2+NYESO, K562-A2+eGFP). As positive control, T cells were stimulated with HLA-A*02:01-transgenic K562 cells loaded with either the SLL-peptide (K562-A2+SLL) or with ivtRNA encoding NY-ESO-1 (K562-A2+NYESO). As a negative control HLA-A*02:01-transgenic K562 were either loaded with irrelevant (K562-A2+irr., FTV) peptide or with ivtRNA encoding eGFP (K562-A2+eGFP). In addition, HLA-A*02:01-transgenic K562 cells were transfected with ivtRNA encoding eGFP combined with long peptides (thus being internally processed by the cell) derived from respective antigens comprising cross-recognized epitopes (K562-A2+#3, K562-A2+ #6, K562-A2+#11, K562-A2+#32, K562-A2+#34, K562-A2+#51) by transgenic T cells expressing either the inventive T11.8-10-17 TCR (CD8_T11.8-10-17) or the benchmark-TCR (CD8_benchmark-TCR).

Figure 6A:
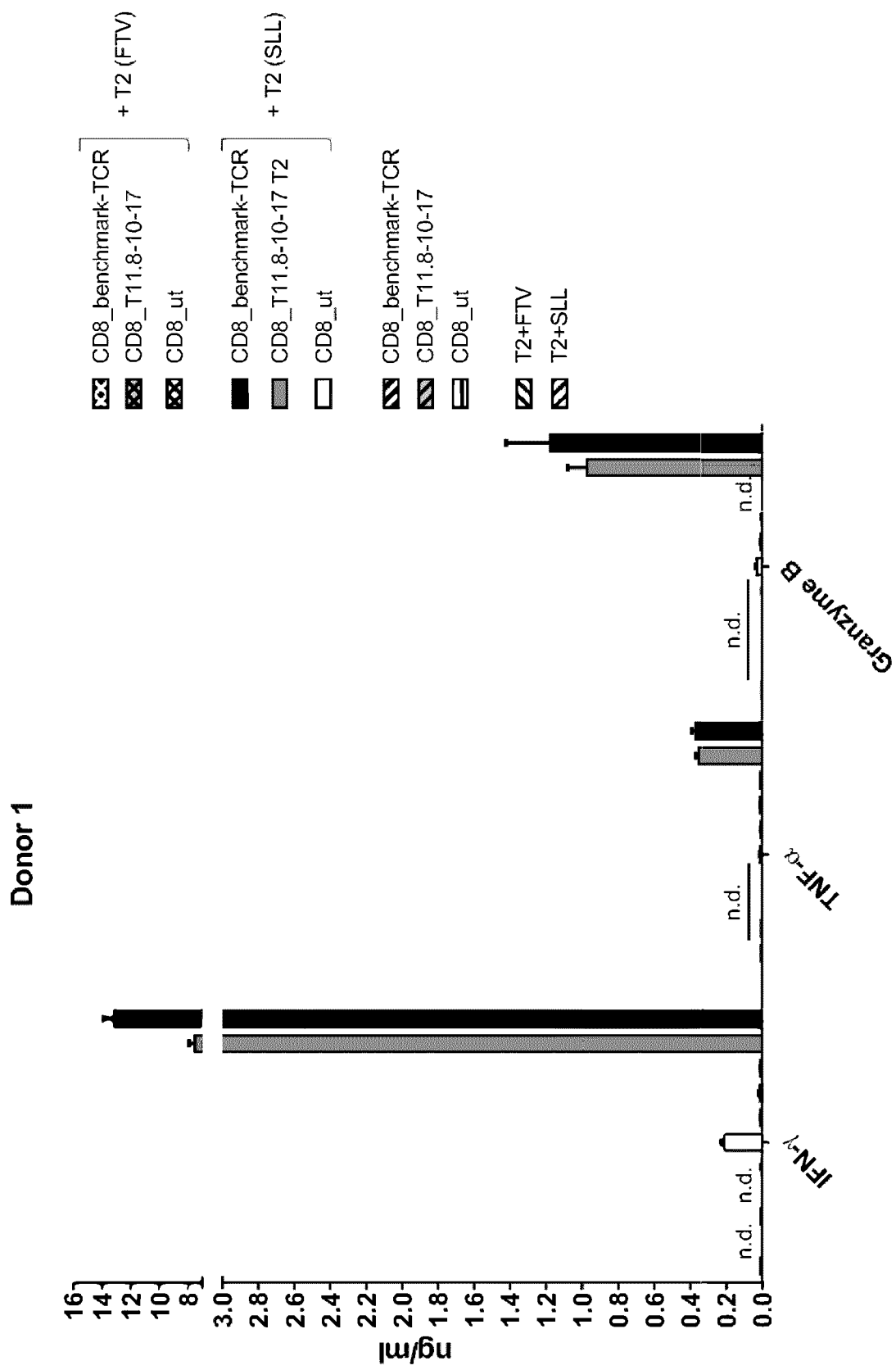
Figure 6B:
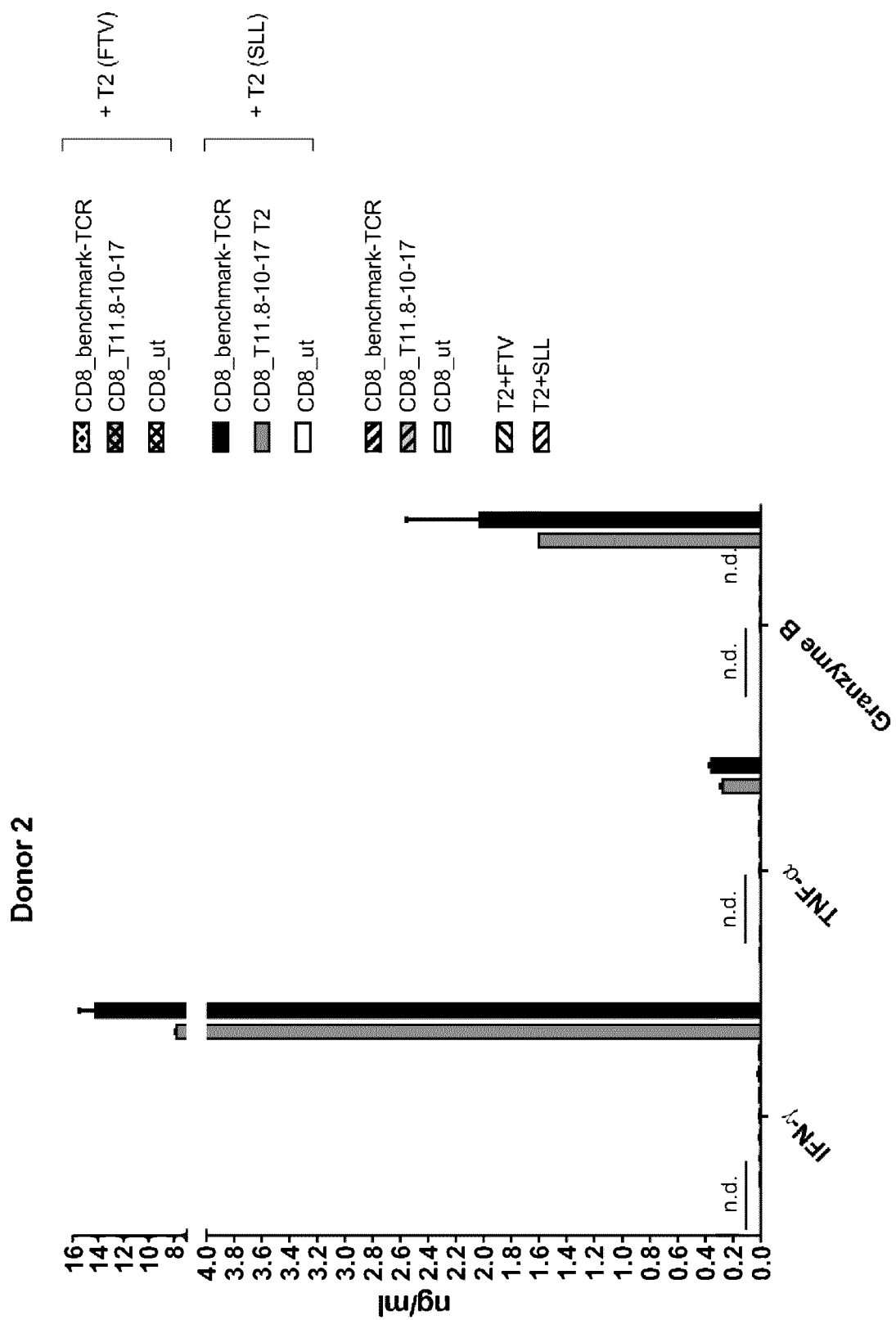

FIGS. 6a and 6b show specific cytokine (IFN-γ, TNF-α) and Granzyme B release, measured in [ng/mL]) of CD8+ enriched PBMC of two different healthy donors (FIG. 6a: Donor 1; FIG. 6b: Donor 2) expressing the NY-ESO-1/LAGE-$1_{157-165}$-specific TCR T11.8-10-17 (CD8_T11.8-10-17) or NY-ESO-1/LAGE-$1_{157-165}$-specific benchmark-TCR (CD8_benchmark-TCR) upon stimulation with HLA-A*02: 01 positive T2 cells loaded with either the NY-ESO-1/LAGE-$1_{157-165}$ (T2(SLL)) peptide or an irrelevant peptide derived from NY-ESO-1 (T2(FTV)). Both transgenic TCRs lead to comparable amounts of IFN-γ, TNF-α and granzyme B secretion by the respective T cells and show a preferable cytokine profile in terms of effector function. As a negative control, T11.8-10-17- or benchmark-transgenic CD8+ T cells were stimulated with HLA-A*02:01 positive FTV-loaded T2 cells (T2(FTV)) or untransduced CD8+ enriched PBMC (CD8_ut) were co-cultured with peptide-loaded T2 cells. No significant cytokine release is measured for all negative controls. Furthermore, T2 cells or T cells cultured alone did not show any background cytokine release. Secretion of IFN-γ, TNF-α and granzyme B by either T11.8-10-17- or benchmark-transgenic CD8+ T cells was determined by multiplex assay using the Milliplex MAP Kit and analyzed by MagPix analyzer.

Figure 7A:
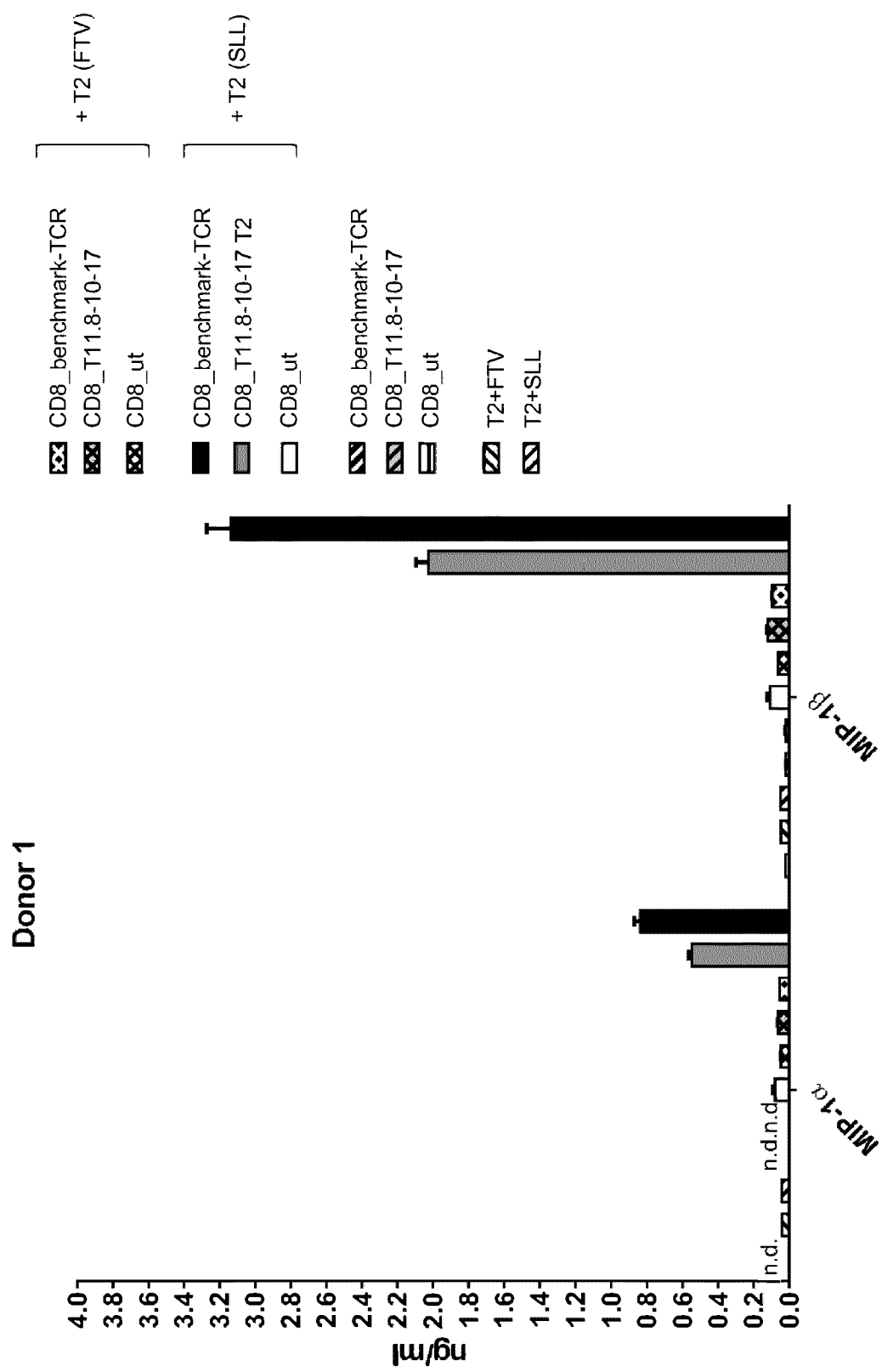
Figure 7B:
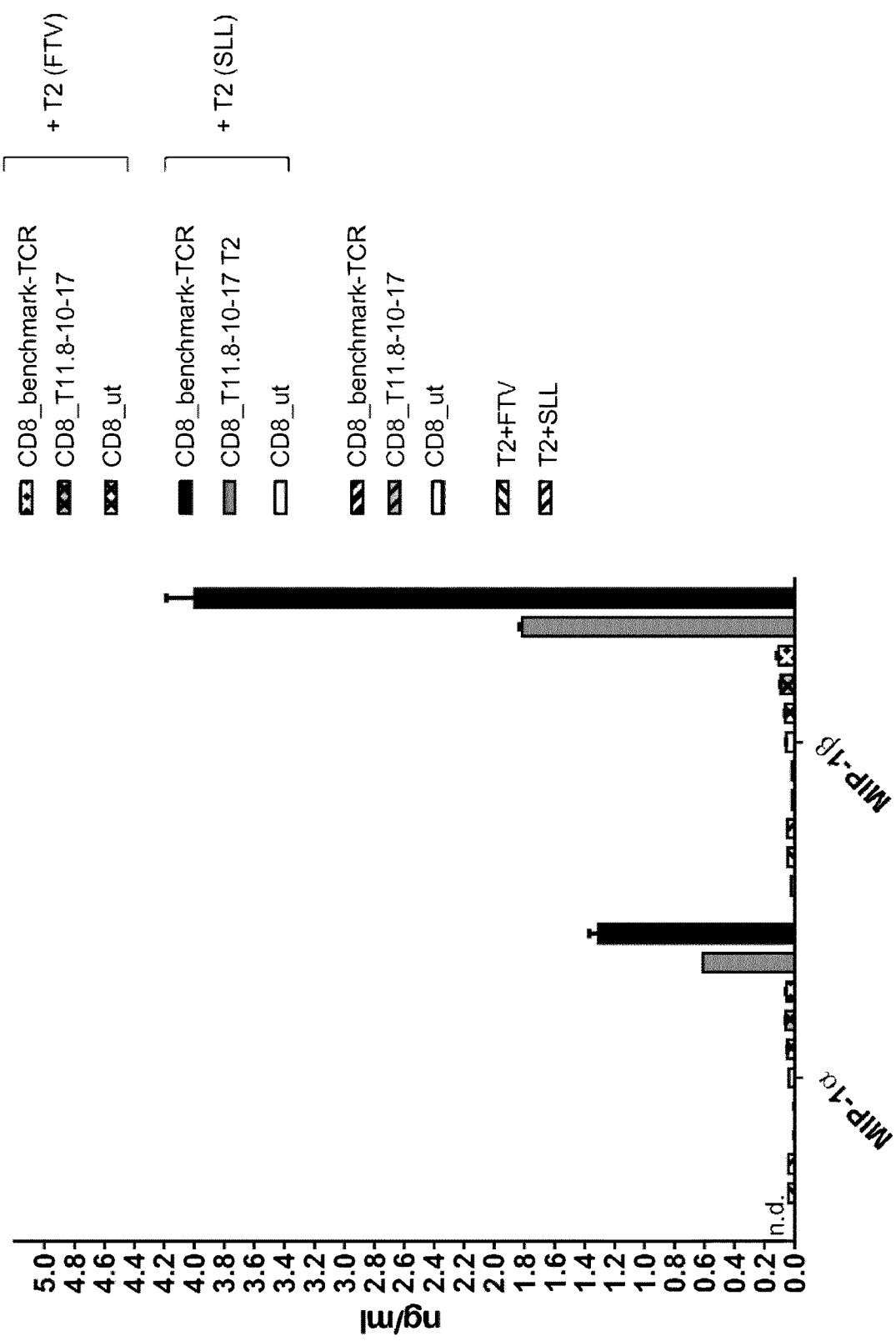

FIGS. 7a and 7b shows specific chemokine release (MIP-1α and MIP-1(3) of CD8+ enriched PBMC (FIG. 7a: Donor 1 or FIG. 7b: Donor 2) expressing the NY-ESO-1/LAGE-$1_{157-165}$-specific TCR T1.8-10-17 (CD8_T11.8-10-17) or NY-ESO-1/LAGE-$1_{157-165}$-specific benchmark-TCR (CD8_benchmark-TCR) upon stimulation with HLA-A*02: 01 positive T2 cells loaded with either the NY-ESO-1/LAGE-$1_{157-165}$ (SLL) peptide (T2(SLL)) or an irrelevant peptide derived from NY-ESO-1 (FTV) (T2(FTV)). The benchmark-TCR transgenic T cells secreted higher amounts of MIP-1α and markedly higher amounts of MIP-1β compared to TCR T11.8-10-17 transgenic T cells upon stimulation with SLL peptide-loaded T2 cells.

As negative control, T11.8-10-17- or benchmark-transgenic CD8+ T cells were stimulated with HLA-A*02:01 positive FTV-loaded T2 cells or untransduced CD8+ enriched PBMC (CD8_ut) were co-cultured with peptide-loaded T2 cells. Negligible chemokine release is measured for all negative controls. Furthermore, T2 cells or T cells cultured alone do not show any chemokine release. Secretion of MIP-1α and MIP-1β by either T11.8-10-17- or benchmark-transgenic CD8+ T cells was determined by multiplex assay using the Milliplex MAP Kit and analyzed by MagPix analyzer.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody which is obtained from this source.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±10%, and preferably of ±5%.

Technical terms are used by their common sense or meaning to the person skilled in the art. If a specific meaning is conveyed to certain terms, definitions of terms will be given in the following in the context of which the terms are used.

TCR Background

A TCR is composed of two different and separate protein chains, namely the TCR alpha (α) and the TCR beta (β) chain. The TCR α chain comprises variable (V), joining (J) and constant (C) regions. The TCR β chain comprises variable (V), diversity (D), joining (J) and constant (C) regions. The rearranged V(D)J regions of both the TCR α and the TCR β chain contain hypervariable regions (CDR, complementarity determining regions), among which the CDR3 region determines the specific epitope recognition. At the C-terminal region both TCR α chain and TCR β chain contain a hydrophobic transmembrane domain and end in a short cytoplasmic tail.

Typically, the TCR is a heterodimer of one α chain and one β chain. This heterodimer can bind to MHC molecules presenting a peptide.

The term "variable TCR α region" or "TCR α variable chain" or "variable domain" in the context of the invention refers to the variable region of a TCR α chain. The term "variable TCR β region" or "TCR β variable chain" in the context of the invention refers to the variable region of a TCR β chain.

The TCR loci and genes are named using the International Immunogenetics (IMGT) TCR nomenclature (IMGT Database, www.IMGT.org; Giudicelli, V., et al., IMGT/LIGM-DB, the IMGT® comprehensive database of immunoglobulin and T cell receptor nucleotide sequences, Nucl. Acids Res., 34, D781-D784 (2006). PMID: 16381979; T cell Receptor Factsbook, LeFranc and LeFranc, Academic Press ISBN 0-12-441352-8).

Target

A first aspect of the invention relates to an isolated T cell receptor (TCR) specific for NY-ESO-1/LAGE-1.

NY-ESO-1/LAGE-1 belongs to the group of so called Cancer/Testis antigens. Cancer/Testis antigens are expressed in various malignant tumors and germ cells but in no other adult tissues. Therefore, NY-ESO-1/LAGE-1 is an interesting immunotherapeutic target antigen. The human gene encoding NY-ESO-1 is designated CTAG1A (ENSGT00000268651), having two isoforms termed CTAG1A-002 and CTAG1A-201 (ENST00000599837 and ENST00000593606) with a copy designated CTAG1B (ENSG0000184033), having two iso forms termed CTAG1B-001 and CTAG1B-002 (ENST00000359887 and ENST00000328435). The human gene encoding LAGE-1 is designated CTAG2.1 (ENSG0000126890) having an isoform designated CATG2.1 and an isoform designated CATG2.2 (ENST0000247306 and ENST0000369585).

In particular, the TCR specifically recognizes the amino acid sequence SEQ ID NO: 1 (LLMWI) or a fragment thereof. More particularly, the TCR specifically recognizes the amino acid sequence SEQ ID NO: 2 (SLLMWI) or a fragment thereof. Even more particularly, the TCR specifically recognizes the amino acid sequence SEQ ID NO: 3 (SLLMWITQC) or a fragment thereof. SEQ ID NOs: 1 to 3 are part of NY-ESO-1 as well as LAGE-1.

Typically, the TCR recognizes the peptide fragment of the antigen when it is presented by a major histocompatibility complex (MHC) molecule.

The human leukocyte antigen (HLA) system or complex is a gene complex encoding the major histocompatibility complex (MHC) proteins in humans. HLA-A*02 is one particular class I major histocompatibility complex (MHC) allele group at the HLA-A locus. HLA-A*02:01 is a specific HLA-A*02 allele.

Thus in a specific embodiment, the TCR specifically recognizes the HLA-A*02 bound form of the amino acid sequence of SEQ ID NO: 1, SEQ ID NO: 2 and/or SEQ ID NO: 3.

In an even more specific embodiment the TCR specifically recognizes the HLA-A*02:01 bound form of the amino acid sequence of SEQ ID NO: 1, SEQ ID NO: 2 and/or SEQ ID NO: 3.

The TCR is highly specific for NY-ESO and exhibits low cross-reactivity to other peptides, such as peptides as set out in SEQ ID NOs: 17-22, in particular when internally processed. In one embodiment, the TCR exhibits substantially no cross-reactivity to peptide SEQ ID NO: 17, in particular when internally processed. In some embodiments the TCR exhibits substantially no cross-reactivity to at least one of the peptides set out in SEQ ID Nos: 17-22, in particular when internally processed. The cross-reactivity may be measured by INFy secretion as described herein.

TCR Specific Sequence

Some embodiments relate to an isolated TCR comprising a TCR α chain and a TCR β chain, wherein
the TCR α chain comprises a complementarity-determining region 3 (CDR3) having the sequence of SEQ ID NO: 6,
the TCR β chain comprises a CDR3 having the amino acid sequence of SEQ ID NO: 9.

Specific embodiments refer to an isolated TCR comprising:
a TCR α chain comprising a CDR1 having the amino acid sequence of SEQ ID NO: 4, a CDR 2 having the amino acid sequence of SEQ ID NO: 5 and a CDR 3 having the sequence of SEQ ID NO: 6.
a TCR β chain comprising a CDR1 having the amino acid sequence of SEQ ID NO: 7, a CDR 2 having the amino acid sequence of SEQ ID NO: 8 and a CDR 3 having the sequence of SEQ ID NO: 9.

In some embodiments, the TCR comprises a variable TCR α region having an amino acid sequence which is at least 80%, at least 85%, at least 90%, at least 95%, at least 96%, at least 97%, at least 98%, at least 99% identical to SEQ ID NO: 10 and a variable TCR β region having an amino acid sequence which is at least 80%, at least 85%, at least 90%, at least 95%, at least 96%, at least 97%, at least 98%, at least 99% identical to SEQ ID NO: 11.

A preferred embodiment relates to a TCR comprising a variable TCR α region having the amino acid sequence of SEQ ID NO: 10 and a variable TCR β region having the amino acid sequence of SEQ ID NO: 11.

The TCR of the T cell clone T11.8-10-17 which is used in the examples comprises a TCR α chain comprising a complementarity-determining region 3 (CDR3) having the sequence of SEQ ID NO: 6 and a TCR β chain comprising a CDR3 having the amino acid sequence of SEQ ID NO: 9. In particular, the inventive TCR comprises a variable TCR α region having the amino acid sequence of SEQ ID NO: 10 and a variable TCR β region having the amino acid sequence of SEQ ID NO: 11.

As can be seen from the Examples the TCRs according to the invention are specific for NYESO-1/LAGE-1 and exhibit only very low cross-reactivity to other epitopes or antigens.

Other embodiments relate to an isolated TCR comprising a TCR α chain having an amino acid sequence which is at least 80%, at least 85%, at least 90%, at least 95%, at least 96%, at least 97%, at least 98%, at least 99% identical to SEQ ID NO: 12 and a TCR β chain having an amino acid sequence which is at least 80%, at least 85%, at least 90%, at least 95%, at least 96%, at least 97%, at least 98%, at least 99% identical to SEQ ID NO: 13.

Specific embodiments refer to a TCR comprising a TCR α chain having the amino acid sequence of SEQ ID NO: 12 and a TCR β chain having the amino acid sequence of SEQ ID NO: 13. Thus, the TCR described herein that is specific for the complex of HLA-A*02:01 with the NY-ESO-1/LAGE-1 peptide of SEQ ID NO: 1, SEQ ID NO: 2 or SEQ ID NO: 3 comprises a Vα chain encoded by the TRAV12-2 gene and a Vβ gene encoded by the TRBV12-4 gene.

Other embodiments refer to an isolated TCR comprising a TCR α chain and a TCR β chain, wherein
the variable TCR α region has an amino acid sequence which is at least 80%, at least 85%, at least 90%, at least 95%, at least 96%, at least 97%, at least 98%, at least 99% identical to SEQ ID NO: 10 and comprises a CDR3 region having the amino acid sequence set out in SEQ ID NO: 6;
the variable TCR β region has an amino acid sequence which is at least 80%, at least 85%, at least 90%, at least 95%, at least 96%, at least 97%, at least 98%, at least 99% identical to SEQ ID NO: 11 and comprises a CDR3 having the amio acid sequence set out in SEQ ID NO: 9.

The determination of percent identity between multiple sequences is preferably accomplished using the AlignX application of the Vector NTI Advance™ 10 program (Invitrogen Corporation, Carlsbad Calif., USA). This program uses a modified Clustal W algorithm (Thompson et al., 1994. Nucl Acids Res. 22: pp. 4673-4680; Invitrogen Corporation; Vector NTI Advance™ 10 DNA and protein sequence analysis software. User's Manual, 2004, pp. 389-662). The determination of percent identity is performed with the standard parameters of the AlignX application.

The TCR according to the invention is isolated or purified. "Isolated" in the context of the invention means that the TCR is not present in the context in which it originally occurred in nature. "Purified" in the context of the invention means e.g. that the TCR is free or substantially free of other proteins and non-protein parts of the cell it originally stems from.

In some embodiments, the amino acid sequence of the TCR may comprise one or more phenotypically silent substitutions.

"Phenotypically silent substitutions" are also named "conservative amino acid substitutions". The concept of "conservative amino acid substitutions" is understood by the skilled artisan, and preferably means that codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. These variations can spontaneously occur, be introduced by random mutagenesis, or can be introduced by directed mutagenesis. Those changes can be made without destroying the essential characteristics of these polypeptides. The ordinarily skilled artisan can readily and routinely screen variant amino acids and/or the nucleic acids encoding them to determine if these variations substantially reduce or destroy the ligand binding capacity by methods known in the art.

The skilled person understands, that also the nucleic acid encoding the TCR may be modified. Useful modifications in the overall nucleic acid sequence include codon optimization of the sequence. Alterations may be made which lead to conservative substitutions within the expressed amino acid sequence. These variations can be made in complementarity determining and non-complementarity determining regions of the amino acid sequence of the TCR chain that do not affect function. Usually, additions and deletions should not be performed in the CDR3 region.

According to some embodiments of the invention the amino acid sequence of the TCR is modified to comprise a detectable label, a therapeutic agent or pharmacokinetic modifying moiety.

Non-limiting examples for detectable labels are radiolabels, fluorescent labels, nucleic acid probes, enzymes and contrast reagents. Therapeutic agents which may be associated with the TCRs include radioactive compounds, immunomodulators, enzymes or chemotherapeutic agents. The therapeutic agents could be enclosed by a liposome linked to TCR so that the compound can be released slowly at the target site. This will avoid damaging during the transport in the body and ensure that the therapeutic agent, e.g. toxin, has maximum effect after binding of the TCR to the relevant antigen presenting cells. Other examples for therapeutic agents are:

peptide cytotoxins, i.e. proteins or peptides with the ability to kill mammalian cells, such as ricin, diphtheria toxin, pseudomonas bacterial exotoxin A, DNase and RNase. Small molecule cytotoxic agents, i.e. compounds with the ability to kill mammalian cells having a molecular weight of less than 700 Daltons. Such compounds could contain toxic metals capable of having a cytotoxic effect. Furthermore, it is to be understood that these small molecule cytotoxic agents also include pro-drugs, i.e. compounds that decay or are converted under physiological conditions to release cytotoxic agents. Such agents may for example include docetaxel, gemcitabine, cis-platin, maytansine derivatives, rachelmycin, calicheamicin, etoposide, ifosfamide, irinotecan, porfimer sodium photofrin II, temozolomide, topotecan, trimetrexate glucoronate, mitoxantrone, auristatin E, vincristine and doxorubicin; radionuclides, such as, iodine 131, rhenium 186, indium 111, yttrium 90. bismuth 210 and 213, actinium 225 and astatine 213. The association of the radionuclides with the TCRs or derivatives thereof may for example be carried out by chelating agents; immunostimulators, also known as immunostimulants, i.e. immune effector molecules which stimulate immune response. Exemplary immunstimulators are cytokines such as IL-2 and IFN-γ, antibodies or fragments thereof, including anti-T cell or NK cell determinant antibodies (e.g anti-CD3, anti-CD28 or anti-CD16); alternative protein scaffolds with antibody like binding characteristics; Superantigens, i.e. antigens that cause non-specific activation of T-cells resulting in polyclonal T cell activation and massive cytokine release, and mutants thereof; chemokines such as IL-8, platelet factor 4, melanoma growth stimulatory protein, etc. complement activators; xenogeneic protein domains, allogeneic protein domains, viral/bacterial protein domains, viral/bacterial peptides.

The antigen receptor molecules (T cell receptor molecules) on human T lymphocytes are non-covalently associated with the CD3 (T3) molecular complex on the cell surface. Perturbation of this complex with anti-CD3 monoclonal antibodies induces T cell activation. Thus, some embodiments refer to a TCR as described herein associated (usually by fusion to an N- or C-terminus of the alpha or beta chain) with an anti-CD3 antibody, or a functional fragment or variant of said anti-CD3 antibody. Antibody fragments and variants/analogues which are suitable for use in the compositions and methods described herein include minibodies, Fab fragments, F(ab<'>)2 fragments, dsFv and scFv fragments, Nanobodies™ (Ablynx (Belgium), molecules comprising synthetic single immunoglobulin variable heavy chain domain derived from a camelid (e.g. camel or llama) antibody) and Domain Antibodies (comprising an affinity matured single immunoglobulin variable heavy chain domain or immunoglobulin variable light chain domain (Domantis (Belgium)) or alternative protein scaffolds that exhibit antibody-like binding characteristics such as Affibodies (comprising engineered protein A scaffold Affibody (Sweden)) or Anticalins (comprising engineered anticalins Pieris (German)).

The therapeutic agent may preferably be selected from the group consisting of an immune effector molecule, a cytotoxic agent and a radionuclide. Preferably, the immune effector molecule is a cytokine.

The pharmacokinetic modifying moiety may be for example at least one polyethylene glycol repeating unit, at least one glycol group, at least one sialyl group or a combination thereof. The association of at least one polyethylene glycol repeating unit, at least one glycol group, at least one sialyl group may be caused in a number of ways known to those skilled in the art. In a preferred embodiment the units are covalently linked to the TCR. The TCRs according to the invention can be modified by one or several pharmacokinetic modifying moieties. In particular, the soluble form of the TCR is modified by one or several pharmacokinetic modifying moieties. The pharmacokinetic modifying moiety may achieve beneficial changes to the pharamacokinetic profile of the therapeutic, for example improved plasma half-life, reduced or enhanced immunogenicity, and improved solubility.

The TCR according to the invention may be soluble or membrane bound. The term "soluble" refers to a TCR being in soluble form (i.e. having no transmembrane or cytoplasmic domains), for example for use as a targeting agent for delivering therapeutic agents to the antigen presenting cell. For stability, soluble αβ heterodimeric TCRs preferably have an introduced disulfide bond between residues of the respective constant domains, as described, for example, in WO 03/020763. One or both of the constant domains present in an αβ heterodimer of the invention may be truncated at the C terminus or C termini, for example by up to 15, or up to 10 or up to 8 or fewer amino acids. For use in adoptive therapy, an αβ heterodimeric TCR may, for example, be transfected as full length chains having both cytoplasmic and transmembrane domains. TCRs may contain a disulfide bond corresponding to that found in nature between the respective alpha and beta constant domains, additionally or alternatively a non-native disulfide bond may be present.

The TCR, in particular a soluble form of the TCR according to the invention can thus be modified by attaching additional functional moieties, e.g. for reducing immunogenicity, increasing hydrodynamic size (size in solution) solubility and/or stability (e.g. by enhanced protection to proteolytic degradation) and/or extending serum half-life.

Other useful functional moieties and modifications include "suicide" or "safety switches" that can be used to shut off effector host cells carrying an inventive TCR in a patient's body. An example is the inducible Caspase 9 (iCasp9) "safety switch" described by Gargett and Brown Front Pharmacol. 2014; 5: 235. Briefly, effector host cells are modified by well-known methods to express a Caspase 9 domain whose dimerization depends on a small molecule dimerizer drug such as AP1903/CIP, and results in rapid induction of apoptosis in the modified effector cells. The system is for instance described in EP2173869 (A2). Examples for other "suicide" "safety switches" are known in the art, e.g. Herpes Simplex Virus thymidine kinase (HSV-TK), expression of CD20 and subsequent depletion using anti-CD20 antibody or myc tags (Kieback et al, Proc Natl Acad Sci USA. 2008 Jan. 15; 105(2):623-8).

TCRs with an altered glycosylation pattern are also envisaged herein. As is known in the art, glycosylation patterns can depend on the amino acid sequence (e.g., the presence or absence of particular glycosylation amino acid residues, discussed below) and/or the host cell or organism in which the protein is produced. Glycosylation of polypeptides is typically either N-linked or O-linked. N-linked refers to the attachment of the carbohydrate moiety to the side chain of an asparagine residue. Addition of N-linked glycosylation sites to the binding molecule is conveniently accomplished by altering the amino acid sequence such that it contains one or more tri-peptide sequences selected from asparagine-X-serine and asparagine-X-threonine (where X is any amino acid except proline). O-linked glycosylation sites may be introduced by the addition of or substitution by, one or more serine or threonine residues to the starting sequence.

Another means of glycosylation of TCRs is by chemical or enzymatic coupling of glycosides to the protein. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. Similarly, deglycosylation (i.e., removal of carbohydrate moieties present on the binding molecule) may be accomplished chemically, e.g. by exposing the TCRs to trifluoromethanesulfonic acid, or enzymatically by employing endo- and exo-glycosidases.

It is also conceivable to add a drug such as a small molecule compound to the TCR, in particular a soluble form of the inventive TCR. Linkage can be achieved via covalent bonds, or non-covalent interactions such as through electrostatic forces. Various linkers, known in the art, can be employed in order to form the drug conjugates. The TCR, in particular a soluble form of the inventive TCR can additionally be modified to introduce additional domains which aid in identification, tracking, purification and/or isolation of the respective molecule (tags). Thus in some embodiments, the TCR α chain or the TCR β chain may be modified to comprise an epitope tag.

Epitope tags are useful examples of tags that can be incorporated into the TCR of the invention. Epitope tags are short stretches of amino acids that allow for binding of a specific antibody and therefore enable identification and tracking of the binding and movement of soluble TCRs or host cells within the patient's body or cultivated (host) cells. Detection of the epitope tag, and hence, the tagged TCR, can be achieved using a number of different techniques.

Tags can further be employed for stimulation and expansion of host cells carrying an inventive TCR by cultivating the cells in the presence of binding molecules (antibodies) specific for said tag.

In general, the TCR can be modified in some instances with various mutations that modify the affinity and the off-rate of the TCR with the target antigen. In particular, the mutations may increase the affinity and/or reduce the off-rate. Thus, the TCR may be mutated in at least one CDR and the variable domain framework region thereof.

However, in a preferred embodiment the CDR regions of the TCR are not modified or in vitro affinity maturated such as for the TCR receptors in the examples. This means that the CDR regions have naturally occurring sequences. This can be advantageous, since in vitro affinity maturation may lead to immunogenicity to the TCR molecule.

This may lead to the production of anti-drug antibodies decreasing or inactivating the therapeutic effect and the treatment and/or induce adverse effects.

The mutation may be one or more substitution(s), deletion(s) or insertions(s). These mutations may be introduced by any suitable method known in the art, such as polymerase chain reaction, restriction enzyme based cloning, ligation independent cloning procedures, which are described for Example in Sambrook, Molecular Cloning—4$^{th}$ Edition (2012) Cold Spring Harbor Laboratory Press.

Theoretically, unpredictable TCR specificity with the risk for cross-reactivity can occur due to mispairing between endogenous and exogenous TCR chains. To avoid mispairing of TCR sequences, the recombinant TCR sequence may be modified to contain minimal murinised Cα and Cβ regions, a technology that has been shown to efficiently enhance correct pairing of several different transduced TCR chains. Murinization of TCRs (i.e. exchanging the human constant regions in the alpha and beta chain by their murine counterparts) is a technique that is commonly applied in order to improve cell surface expression of TCRs in host cells. Without wishing to be bound by specific theory, it is thought that murinized TCRs associate more effectively with CD3 co-receptors; and/or that preferentially pair with each other and are less prone to form mixed TCRs on human T cells genetically modified ex vivo to express the TCRs of desired antigenic specificity, but still retaining and expressing their "original" TCRs.

Nine amino acids responsible for the improved expression of murinized TCRs have been identified (Sommermeyer and Uckert, J Immunol. 2010 Jun. 1; 184(11):6223-31) and it is envisaged to substitute one or all of the amino acid residues in the TCRs alpha and/or beta chain constant region for their murine counterpart residues. This technique is also referred to as "minimal murinization", and offers the advantage of enhancing cell surface expression while, at the same time, reducing the number of "foreign" amino acid residues in the amino acid sequence and, thereby, the risk of immunogenicity.

Some embodiments refer to an isolated TCR as described herein, wherein the TCR is of the single chain type, wherein the TCR α chain and the TCR β chain are linked by a linker sequence.

A suitable single chain TCR form comprises a first segment constituted by an amino acid sequence corresponding to a variable TCR α region, a second segment constituted by an amino acid sequence corresponding to a variable TCR β region fused to the N terminus of an amino acid sequence corresponding to a TCR β chain constant region extracellular sequence, and a linker sequence linking the C terminus of the first segment to the N terminus of the second segment. Alternatively the first segment may be constituted by an amino acid sequence corresponding to a TCR β chain variable region, the second segment may be constituted by an amino acid sequence corresponding to a TCR α chain variable region sequence fused to the N terminus of an amino acid sequence corresponding to a TCR α chain constant region extracellular sequence. The above single chain TCRs may further comprise a disulfide bond between the first and second chains, and wherein the length of the linker sequence and the position of the disulfide bond being such that the variable domain sequences of the first and second segments are mutually orientated substantially as in native T cell receptors. More specifically the first segment may be constituted by an amino acid sequence corresponding to a TCR α chain variable region sequence fused to the N terminus of an amino acid sequence corresponding to a TCR α chain constant region extracellular sequence, the second segment may be constituted by an amino acid sequence corresponding to a TCR β chain variable region fused to the N terminus of an amino acid sequence corresponding to TCR β chain constant region extracellular sequence, and a disulfide bond may be provided between the first and second chains. The linker sequence may be any sequence which does not impair the function of the TCR.

In the context of the present invention, a "functional" TCR α and/or β chain fusion protein shall mean a TCR or TCR variant, for example modified by addition, deletion or substitution of amino acids, that maintains at least substantial biological activity. In the case of the α and/or β chain of a TCR, this shall mean that both chains remain able to form a T-cell receptor (either with a non-modified α and/or β chain or with another inventive fusion protein α and/or β chain) which exerts its biological function, in particular binding to the specific peptide-MHC complex of said TCR, and/or functional signal transduction upon specific peptide:MHC interaction.

In specific embodiments the TCR may be modified, to be a functional T-cell receptor (TCR) α and/or β chain fusion protein, wherein said epitope-tag has a length of between 6 to 15 amino acids, preferably 9 to 11 amino acids. In another embodiment the TCR may be modified to be a functional T-cell receptor (TCR) α and/or β chain fusion protein wherein said T-cell receptor (TCR) α and/or β chain fusion protein comprises two or more epitope-tags, either spaced apart or directly in tandem. Embodiments of the fusion protein can contain 2, 3, 4, 5 or even more epitope-tags, as long as the fusion protein maintains its biological activity/activities ("functional").

Preferred is a functional T-cell receptor (TCR) α and/or β chain fusion protein according to the present invention, wherein said epitope-tag is selected from, but not limited to, CD20 or Her2/neu tags, or other conventional tags such as a myc-tag, FLAG-tag, T7-tag, HA (hemagglutinin)-tag, His-tag, S-tag, GST-tag, or GFP-tag. myc, T7, GST, GFP tags are epitopes derived from existing molecules. In contrast, FLAG is a synthetic epitope tag designed for high antigenicity (see, e.g., U.S. Pat. Nos. 4,703,004 and 4,851,341). The myc tag can preferably be used because high quality reagents are available to be used for its detection. Epitope tags can of course have one or more additional functions, beyond recognition by an antibody. The sequences of these tags are described in the literature and well known to the person of skill in art.

TCR Variants

Another aspect of the invention refers to a polypeptide comprising a functional portion of the TCR of as described herein, wherein the functional portion comprises at least one of the amino acid sequences of SEQ ID NOs: 6 and 9.

The functional portion may mediate the binding of the TCR to the antigen, in particular to the antigen-MHC complex.

In one embodiment, the functional portion comprises the TCR α variable chain and/or the TCR β variable chain as described herein.

The TCR variant molecule may have the binding properties of the TCR receptor but may be combined with signaling domains of effectors cells (other than T cells), in particular with signaling domains of NK cells. Therefore, some embodiments refer to a protein comprising a functional portion of the TCR as described herein in combination with the signaling domains of an effector cell, such as a NK cell.

Another aspect of the invention refers to a multivalent TCR complex comprising at least two TCRs as described herein. In one embodiment of this aspect, at least two TCR molecules are linked via linker moieties to form multivalent complexes. Preferably, the complexes are water soluble, so the linker moiety should be selected accordingly. It is preferable that the linker moiety is capable of attaching to defined positions on the TCR molecules, so that the structural diversity of the complexes formed is minimized. One embodiment of the present aspect is provided by a TCR complex of the invention wherein the polymer chain or peptidic linker sequence extends between amino acid residues of each TCR which are not located in a variable region sequence of the TCR. Since the complexes of the invention may be for use in medicine, the linker moieties should be chosen with due regard to their pharmaceutical suitability, for example their immunogenicity. Examples of linker moieties which fulfil the above desirable criteria are known in the art, for example the art of linking antibody fragments.

Examples for linkers are hydrophilic polymers and peptide linkers. An example for hydrophilic polymers are polyalkylene glycols. The most commonly used of this class are based on polyethylene glycol or PEG. However, others are based on other suitable, optionally substituted, polyalkylene glycols which include polypropylene glycol, and copolymers of ethylene glycol and propylene glycol. Peptide linkers are comprised of chains of amino acids, and function to produce simple linkers or multimerization domains onto which TCR molecules can be attached.

One embodiment refers to a multivalent TCR complex, wherein at least one of said TCRs is associated with a therapeutic agent.

Cytokine and Chemokine Release

Some embodiments refer to the isolated TCR as described herein, polypeptide as described herein, multivalent TCR complex as described herein, wherein IFN-γ secretion is induced by binding of the inventive TCR expressed on an effector cell to the HLA-A*02 bound form of the amino acid sequence selected from the group consisting of SEQ ID NOs: 1 to 3.

The IFN-γ secretion induced by binding of the inventive TCR expressed on an effector cell to the HLA-A*02 bound form of the amino acid sequence selected from the group consisting of SEQ ID NOs: 1 to 3 may be more than 3 ng/ml, such as more than 4 ng/ml, more than 5 ng/ml, more preferably more than 6 ng/ml, most preferably even more than 7 ng/ml. The IFN-γ secretion may be at least 4 times higher when binding to the HLA-A*02 bound form of the amino acid sequence selected from the group consisting of SEQ ID NOs: 1 to 3 compared to binding to the HLA-A*02 bound form of an irrelevant peptide (e.g. SEQ ID No: 15 or 16).

The cytokine and chemokine release, such as IFN-γ secretion and MIP-1α and MIP-1β secretion may be measured by an in vitro assay in which T2 cells transfected with ivtRNA coding one of the amino acid sequences selected from the group consisting of SEQ ID NOs: 1 to 3, preferably SEQ ID NO: 3, are incubated with CD8+ enriched PBMC expressing the TCR to be investigated or using T2 cells loaded with either the NY-ESO-1/LAGE-1$_{157-165}$ (SLL) peptide or an irrelevant peptide derived from NY-ESO-1.

Some embodiments refer to an isolated TCR as described herein, polypeptide as described herein or multivalent TCR complex as described herein, wherein MIP-1α and MIP-1β secretion induced by binding of the inventive TCR expressed on an effector cell to the amino acid sequence selected from the group consisting of SEQ ID NOs: 1 to 3 or the HLA-A*02 bound form thereof is below a predefined threshold. The threshold may be determined by using a specific effector to target ratio of at least 1:1.

The MIP-1α secretion in vitro induced by binding of the inventive TCR expressed on an effector cell to the HLA-A*02 bound form of amino acid sequence selected from the group consisting of SEQ ID NOs: 1 to 3 may be less than 1 ng/ml, preferably less than 0.8 ng/ml, more preferably less than 0.7 ng/ml at a transgenic TCR$^+$ effector cell to target cell ratio of at least 1:1 using 10,000 cells each. The MIP-1β secretion induced by binding to the HLA-A*02 bound form of amino acid sequence selected from the group consisting of SEQ ID NOs: 1 to 3 may be less than 3 ng/ml, preferably less than 2.8 ng/ml, more preferably less than 2.5 ng/ml at a transgenic TCR$^+$ effector to target ratio of at least 1:1 using 10,000 cells each.

The "effector cell" may be a peripheral blood lymphocyte (PBL) or a peripheral blood mononuclear cell (PBMC). Typically, the effector cell is an immune effector cell, especially a T cell. Other suitable cell types include gamma-delta T cells and NK-like T cells.

The MIP-1α secretion may be at most 15 times higher, preferably at most 10 times higher when binding to the HLA-A*02 bound form of the amino acid sequence selected from the group consisting of SEQ ID NOs: 1 to 3 compared to binding to the HLA-A*02 bound form of an irrelevant peptide (e.g. SEQ ID No: 15 or 16). The MIP-1β secretion may be at most 30 times higher, preferably at most 25 times higher when binding to the HLA-A*02 bound form of the amino acid sequence selected from the group consisting of SEQ ID NOs: 1 to 3 compared to binding to the HLA-A*02 bound form of an irrelevant peptide (e.g. SEQ ID No: 15 or 16).

The invention relates also to methods for identifying a TCR or a fragment thereof that binds to the target amino acid sequences selected from SEQ ID NOs: 1 to 3 or the HLA-A*02, preferably or the HLA-A*02:01 bound form thereof, wherein the method comprises contacting the candidate TCR or fragment thereof with the amino acid sequences selected from SEQ ID NOs: 1 to 3 or the HLA-A*02, preferably or the HLA-A*02:01 bound form thereof and determining whether the candidate TCR or fragment thereof binds to the target and/or mediates an immune response. Whether the candidate TCR or fragment thereof mediates an immune response can be determined for example by the measurement of cytokine secretion, such as IFN-γ secretion. As described above cytokine secretion may be measured by an in vitro assay in which K562 cells (or other APCs) transfected with ivtRNA coding one of the amino acid sequences selected from the group consisting of SEQ ID NOs: 1 to 3, preferably SEQ ID NO: 3, are incubated with CD8+ enriched PBMC expressing the TCR or a molecule comprising a fragment of the TCR to be investigated.

Nucleic Acids, Vectors

Another aspect of the invention refers to a nucleic acid encoding a TCR as described herein or encoding the polynucleotide encoding a TCR as described herein.

"Nucleic acid molecule" and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. Preferably, the nucleic acids described herein are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acids can be constructed based on chemical synthesis and/or enzymatic ligation reactions using procedures known in the art or commercially available (e.g. from Genscript, Thermo Fisher and similar companies). See, for example, Sambrook et al. for example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). The nucleic acid can comprise any nucleotide sequence which encodes any of the recombinant TCRs, polypeptides, or proteins, or functional portions or functional variants thereof.

The present disclosure also provides variants of the isolated or purified nucleic acids wherein the variant nucleic acids comprise a nucleotide sequence that has at least 75%, 80%, 81%, 82%, 83%, 84%, 85%, 86%, 87%, 88%, 89%, 90%, 91%, 92%, 93%, 94%, 95%, 96%, 97%, 98%, or 99% identical to the nucleotide sequence encoding the TCR described herein. Such variant nucleotide sequence encodes a functional TCR that specifically recognizes NY-ESO1/LAGE-1.

The disclosure also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the TCRs described herein. It is generally appreciated that conditions can be rendered more stringent by the addition of increasing amounts of formamide.

As already described elsewhere herein, the nucleic acid encoding the TCR may be modified. Useful modifications in the overall nucleic acid sequence may be codon optimization. Alterations may be made which lead to conservative substitutions within the expressed amino acid sequence. These variations can be made in complementarity determining and non-complementarity determining regions of the amino acid sequence of the TCR chain that do not affect function. Usually, additions and deletions should not be performed in the CDR3 region.

Another embodiment refers to a vector comprising the nucleic acid encoding the TCR as described herein.

The vector is preferably a plasmid, shuttle vector, phagemide, cosmid, expression vector, retroviral vector, adenoviral vector or particle and/or vector to be used in gene therapy.

A "vector" is any molecule or composition that has the ability to carry a nucleic acid sequence into a suitable host cell where synthesis of the encoded polypeptide can take place. Typically, and preferably, a vector is a nucleic acid that has been engineered, using recombinant DNA techniques that are known in the art, to incorporate a desired nucleic acid sequence (e.g. a nucleic acid of the invention). The vector may comprise DNA or RNA and/or comprise liposomes. The vector may be a plasmid, shuttle vector, phagemide, cosmid, expression vector, retroviral vector, lentiviral vector, adenoviral vector or particle and/or vector to be used in gene therapy. A vector may include nucleic acid sequences that permit it to replicate in a host cell, such as an origin of replication. A vector may also include one or more selectable marker genes and other genetic elements known to those of ordinary skill in the art. A vector preferably is an expression vector that includes a nucleic acid according to the present invention operably linked to sequences allowing for the expression of said nucleic acid.

Preferably, the vector is an expression vector. More preferably, the vector is a retroviral, more specifically a gamma-retroviral or lentiviral vector.

Cells, Cell Lines

Another aspect of the invention refers to a cell expressing the TCR as described herein.

In some embodiments, the cell is isolated or non-naturally occurring.

In specific embodiments, the cell may comprise the nucleic acid encoding the TCR as described herein or the vector comprising said nucleic acid.

In the cell the above described vector comprising a nucleic acid sequence coding for the above described TCR may be introduced or ivtRNA coding for said TCR may be introduced. The cell may be a peripheral blood lymphocyte such as a T cell. The method of cloning and exogenous expression of the TCR is for example described in Engels et al. (Relapse or eradication of cancer is predicted by peptide-major histocompatibility complex affinity. Cancer Cell, 23(4), 516-26. 2013). The transduction of primary human T cells with a lentiviral vector is, for example, described in Cribbs "simplified production and concentration of lentiviral vectors to achieve high transduction in primary human T cells" BMC Biotechnol. 2013; 13: 98.

The term "transfection" and "transduction" are interchangeable and refer to the process by which an exogenous nucleic acid sequence is introduced in a host cell, e.g. in an eukaryotic host cell. It is noted that introduction or transfer of nucleic acid sequences is not limited to the mentioned methods but can be achieved by any number of means including electroporation, microinjection, gene gun delivery, lipofection, superfection and the mentioned infection by retroviruses or other suitable viruses for transduction or transfection.

Some embodiments refer to a cell comprising:
a) an expression vector which comprises at least one nucleic acid as described herein, or
b) a first expression vector which comprises a nucleic acid encoding the alpha chain of the TCR as described herein, and a second expression vector which comprises a nucleic acid encoding the beta chain of a TCR as described herein.

In some embodiments, the cell is a peripheral blood lymphocyte (PBL) or a peripheral blood mononuclear cell (PBMC). The cell may be a natural killer cell or a T cell. Preferably, the cell is a T cell. The T cell may be a CD4+ or a CD8+ T cell. In some embodiments the cell is a stem cell like memory T cell.

Stem cell-like memory T cells (TSCM) are a less-differentiated subpopulation of CD8+ T cells, which are characterized by the capacity of self-renewal and to persist long-term. Once these cells encounter their antigen in vivo, they differentiate further into central memory T cells (TCM), effector memory T cells (TEM) and terminally differentiated effector memory T cells (TEMRA) with some TSCM remaining quiescent (Flynn et al., Clinical & Translational Immunology (2014). These remaining TSCM cells show the capacity to build a durable immunological memory in vivo and therefore are considered an important T cell subpopulation for adoptive T cell therapy (Lugli et al., Nature Protocols 8, 33-42 (2013) Gattinoni et al., Nat. Med. 2011 October; 17(10): 1290-1297). Immune-magnetic selection can be used in order to restrict the T cell pool to the stem cell memory T cell subtype see (Riddell et al. 2014, Cancer Journal 20(2): 141-44)

Antibodies Targeting TCR

Another aspect of the invention refers to an antibody or antigen binding fragment thereof specifically binding to a portion of the TCR as described herein that mediates specificity for NY-ESO-1/LAGE-1. In one embodiment, the portion of the TCR that mediates the NY-ESO-1/Lage-1 specificity comprises the CDR3 of the alpha chain of SEQ ID NO: 6 and/or the CDR3 of the beta chain of SEQ ID NO: 9.

The antibody antigen binding fragment may modulate the activity of the TCR. It may block or may not block the binding of the TCR with NY-ESO. It could be used for modulating the therapeutic activity of the TCR or for diagnostic purposes.

Pharmaceutical Compositions, Medical Treatments and Kits

Another aspect of the invention refers to pharmaceutical composition comprising the TCR as described herein, the polypeptide comprising a functional portion of said TCR, the multivalent TCR complex as described herein, the nucleic acid encoding the TCR, the vector comprising said nucleic acid, the cell comprising said TCR, or the antibody specifically binding to a portion of the TCR as described herein.

Those active components of the present invention are preferably used in such a pharmaceutical composition, in doses mixed with an acceptable carrier or carrier material, that the disease can be treated or at least alleviated. Such a composition can (in addition to the active component and the carrier) include filling material, salts, buffer, stabilizers, solubilizers and other materials, which are known state of the art.

The term "pharmaceutically acceptable" defines a nontoxic material, which does not interfere with effectiveness of the biological activity of the active component. The choice of the carrier is dependent on the application.

The pharmaceutical composition may contain additional components which enhance the activity of the active component or which supplement the treatment. Such additional components and/or factors can be part of the pharmaceutical composition to achieve synergistic effects or to minimize adverse or unwanted effects.

Techniques for the formulation or preparation and application/medication of active components of the present invention are published in "Remington's Pharmaceutical Sciences", Mack Publishing Co., Easton, Pa., latest edition. An appropriate application is a parenteral application, for example intramuscular, subcutaneous, intramedular injections as well as intrathecal, direct intraventricular, intravenous, intranodal, intraperitoneal or intratumoral injections. The intravenous injection is the preferred treatment of a patient.

According to a preferred embodiment, the pharmaceutical composition is an infusion or an injection.

An injectable composition is a pharmaceutically acceptable fluid composition comprising at least one active ingredient, e.g. an expanded T cell population (for example autologous or allogenic to the patient to be treated) expressing a TCR. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this disclosure are conventional; appropriate formulations are well known to those of ordinary skill in the art.

Typically, the pharmaceutical composition comprises at least one pharmaceutically acceptable carrier.

Accordingly, another aspect of the invention refers to the TCR as described herein, the polypeptide comprising a functional portion of said TCR, the multivalent TCR complex according as described herein, the nucleic acid encoding said TCR, the vector comprising said nucleic acid, the cell comprising said TCR, or the antibody specifically binding to a portion of the TCR as described herein for use as a medicament.

Some embodiments refer to the TCR as described herein, the polypeptide comprising a functional portion of said TCR, the multivalent TCR complex according as described herein, the nucleic acid encoding said TCR, the vector comprising said nucleic acid, the cell comprising said TCR for use in the treatment of cancer.

In one embodiment the cancer is a hematological cancer or a solid tumor.

Hematological cancers also called blood cancers which do not form solid tumors and therefore are dispersed in the body. Examples of hematological cancers are leukemia, lymphoma or multiple myeloma. There are two major types of solid tumors, sarcomas and carcinomas. Sarcomas are for example tumors of the blood vessel, bone, fat tissue, ligament, lymph vessel, muscle or tendon.

In one embodiment, the cancer is selected from the group consisting of sarcoma, prostate cancer, uterine cancer, thyroid cancer, testicular cancer, renal cancer, pancreatic cancer, ovarian cancer, esophageal cancer, non-small-cell lung cancer, non-Hodgkin's lymphoma, multiple myeloma, melanoma, hepatocellular carcinoma, head and neck cancer, gastric cancer, endometrial cancer, colorectal cancer, cholangiocarcinoma, breast cancer, bladder cancer, myeloid leukemia and acute lymphoblastic leukemia. Preferably, the cancer is sarcoma or osteosarcoma.

The TCRs particularly well recognize osteosarcoma and melanoma, such as the osteosarcoma cell line SAOS-2 and the melanoma cell lines MM415 and Me1624.38.

Also contemplated herein are pharmaceutical compositions and kits containing one or more of (i) an isolated TCR as described herein; (ii) viral particles comprising a nucleic acid encoding a recombinant TCR; (iii) immune cells, such as T cells or NK cells, modified to express a recombinant TCR as described herein; (iv) nucleic acids encoding a recombinant TCR as described herein. In some embodiments, the present disclosure provides compositions comprising lentiviral vector particles comprising a nucleotide sequence encoding a recombinant TCR described herein (or T cells that have been modified using the vector particles described herein to express a recombinant TCR). Such compositions can be administered to subjects in the methods of the present disclosure as described further herein.

Compositions comprising the modified T cells as described herein can be utilized in methods and compositions for adoptive immunotherapy in accordance with known techniques, or variations thereof that will be apparent to those skilled in the art based on the instant disclosure.

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

The number of cells for an effective treatment in the composition is typically greater than 10 cells, and up to $10^6$, up to and including $10^8$ or $10^9$ cells and can be more than $10^{19}$ cells. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 ml or less, even 250 ml or 100 ml or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^9$, $10^{10}$ or $10^{11}$ cells. Pharmaceutical compositions provided herein can be in various forms, e.g., in solid, liquid, powder, aqueous, or lyophilized form. Examples of suitable pharmaceutical carriers are known in the art. Such carriers and/or additives can be formulated by conventional methods and can be administered to the subject at a suitable dose. Stabilizing agents such as lipids, nuclease inhibitors, polymers, and chelating agents can preserve the compositions from degradation within the body. In a composition intended to be administered by injection, one or more of a surfactant, preservative, wetting agent, dispersing agent, suspending agent, buffer, stabilizer and isotonic agent may be included.

The recombinant TCRs as described herein, or the viral vector particles comprising a nucleotide sequence encoding an recombinant TCR provided herein, can be packaged as kits. Kits can optionally include one or more components such as instructions for use, devices, and additional reagents, and components, such as tubes, containers and syringes for practice of the methods. Exemplary kits can include the nucleic acids encoding the recombinant TCRs, the recombinant TCR polypeptides, or viruses provided herein, and can optionally include instructions for use, a device for detecting a virus in a subject, a device for administering the compositions to a subject, and a device for administering the compositions to a subject.

Kits comprising polynucleotides encoding a gene of interest (e.g., a recombinant TCR) are also contemplated herein. Kits comprising a viral vector encoding a sequence of interest (e.g., a recombinant TCR) and optionally, a polynucleotide sequence encoding an immune checkpoint inhibitor are also contemplated herein.

Kits contemplated herein also include kits for carrying out the methods for detecting the presence of polynucleotides encoding any one or more of the TCRs disclosed herein. In particular, such diagnostic kits may include sets of appropriate amplification and detection primers and other associated reagents for performing deep sequencing to detect the polynucleotides encoding TCRs disclosed herein disclosed herein. In further embodiments, the kits herein may comprise reagents for detecting the TCRs disclosed herein, such as antibodies or other binding molecules. Diagnostic kits may also contain instructions for determining the presence of the polynucleotides encoding the TCRs disclosed herein or for determining the presence of the TCRs disclosed herein. A kit may also contain instructions. Instructions typically include a tangible expression describing the components included in the kit, and methods for administration, including methods for determining the proper state of the subject, the proper dosage amount, and the proper administration method. Instructions can also include guidance for monitoring the subject over the duration of the treatment time.

Kits provided herein also can include a device for administering a composition described herein to a subject. Any of a variety of devices known in the art for administering medications or vaccines can be included in the kits provided herein. Exemplary devices include, but are not limited to, a hypodermic needle, an intravenous needle, a catheter, a needle-less injection device, an inhaler, and a liquid dispenser, such as an eyedropper. Typically, the device for administering a virus of the kit will be compatible with the virus of the kit; for example, a needle-less injection device such as a high pressure injection device can be included in kits with viruses not damaged by high pressure injection, but is typically not included in kits with viruses damaged by high pressure injection.

Kits provided herein also can include a device for administering a compound, such as a T cell activator or stimulator, or a TLR agonist, such as a TLR4 agonist to a subject. Any of a variety of devices known in the art for administering medications to a subject can be included in the kits provided herein. Exemplary devices include a hypodermic needle, an intravenous needle, a catheter, a needle-less injection, but are not limited to, a hypodermic needle, an intravenous needle, a catheter, a needle-less injection device, an inhaler, and a liquid dispenser such as an eyedropper. Typically, the device for administering the compound of the kit will be compatible with the desired method of administration of the compound.

EXPERIMENTS

Examples

Example 1: Isolation of
NY-ESO-1/LAGE-1-Specific T Cell Clone

An in vitro priming approach to isolate T cell clones of any desired MHC restriction and antigen specificity was used. The priming system uses mature dendritic cells (mDCs) of an HLA-A*02:01 negative donor as antigen-presenting cells and autologous CD8$^+$-enriched T cells as responding cells. In vitro transcribed RNA (ivtRNA) encoding the full-length human CTAG1A/B amino acid sequence as referenced in SEQ ID NO:14 serves as the source of specific antigen. Simultaneously, human HLA-A*02:01-encoding ivtRNA is used as source of restriction element transfected into mDCs to set-up an allogeneic priming in terms of this dedicated HLA allele (as described in WO2007/017201). After electroporation into the mDCs, the CTAG1-encoding ivtRNA is translated into full-length protein, which is subsequently processed and presented as peptides by transgenic HLA-A*02:01 molecules which are expressed by transfected mDCs. In vitro co-cultures of T cells with the ivtRNA-transfected mDCs from the same donor lead to de novo induction of antigen-specific T cells that serve as the source of corresponding TCRs. Antigen-specific T cells can be enriched by a variety of methods and are cloned by limiting dilution or FACS-based single cell sorting.

Example 1.1: Allogeneic Priming Approach Using
Mature Dendritic Cells Transfected with
HLA-A*02:01-Encoding ivtRNA Dendritic cell priming of T cells with high-affinity TCR was accomplished using peptide presentation by allogeneic HLA-A*02:01 molecules according to the following protocol:

HLA-A*02:01/CTAG1 Priming

Mature dendritic cells were produced (8 days mDCs) using suitable maturation cocktails according to Jonuleit et al. for DCs (Jonuleit et al. 1997, Eur. J. Immunol. 1997, 27:3135-3142)

Antigen presenting cells (8 day matured mDCs) were derived from healthy donors and electroporated with 20 µg ivtRNA coding for the desired antigen and HLA molecule (HLA-A*02:01). The prepared mDCs were subsequently co-cultured with CD8$^+$ enriched PBMC of a healthy donor in a ratio of 1:10 for about 14 days in a suitable cell medium supplemented with IL-2 (50 units/ml every second day) at 37° C. (6% $CO_2$). Subsequently, NY-ESO-1/LAGE-$1_{157-165}$ specific cells were identified using HLA-A*02: 01 NY-ESO-1/LAGE-$1_{157-165}$ multimers (ProImmune) and subsequently separated by single cell sorting using FACS technology.

Example 2: Function/Specificity Analyses

Following the identification of a candidate TCR (T11.8-10-17) that binds to the desired NY-ESO-1/LAGE-1 epitope (NY-ESO-1/LAGE-$1_{157-165}$) on HLA-A2, full characterization regarding function and specificity was conducted. Analyses confirmed specificity of the T cell clone T11.8-10-17 for NY-ESO-1, more precisely NY-ESO-1/LAGE-$1_{157-165}$ (FIG. 1), the capacity of T11.8-10-17-transduced CD8$^+$ enriched T cells to specifically lyse HLA-A2 positive NY-ESO-1/LAGE-$1_{157-165}$ peptide-loaded tumor cell lines (FIG. 2) and tumor cell recognition of T11.8-10-17 transduced CD8$^+$ enriched T cells in co-culture with various human tumor cell lines (FIG. 3).

Example 2.1: Analysis of the Original T Cell Clone T11.8-10-17

Example 2.1.1: Antigen-specificity

Experimental Layout: Stimulation by ivtRNA-Loaded K562 or Peptide-Loaded T2 Cells NY-ESO-1/LAGE-$1_{157-165}$ specificity was confirmed according to the following protocol: A standard sandwich ELISA analysis was performed, detecting IFN-γ (BD human IFN-γ ELISA set).

As target cells, T2 cells (HLA-A*02$^{pos}$) were loaded with saturating amounts ($10^{-5}$ M) of NY-ESO-1/LAGE-$1_{157-165}$ peptide ("SLL peptide"; SEQ ID NO: 3) or irrelevant NY-ESO-1-derived peptide ("FTV peptide"; SEQ ID NO. 15), i.e. FTVSGNILTI peptide ("FTV peptide") or RLLEFYLAM peptide ("RLL peptide", SEQ ID NO. 16). In addition, K562 cells (transduced with HLA-A*02:01; "K562-A2") were transfected with 20 µg ivtRNA encoding NY-ESO-1/LAGE-$1_{157-165}$ or electroporated with water as control. Each target cell line was co-cultured with the T cell clone T11.8-10-17 at a ratio of about 2:1 using 20,000 target cells and 10,000 T cells. IFN-γ was detected by standard sandwich ELISA (BD human IFN-γ ELISA set).

Results

The candidate clone secreted IFN-γ only upon stimulation with NY-ESO-1 expressing K562-A2 cells or SLL-peptide loaded T2 cells but not in combination with water electroporated K562-A2 or T2 cells loaded with irrelevant peptides (FVT or RLL) (FIG. 1).

Example 2.2: Recognition of Tumor Cells

Experimental Layout: Killing of Tumor Cells

The killing capacity of T11.8-10-17- or benchmark-TCR-transduced CD8$^+$ T cells (CD8-T11.8-10-17 or CD8 benchmark-TCR) was evaluated by co-culturing with the HLA-A*02 positive NY-ESO-1/LAGE-1 positive tumor cell line Me1624.38 (FIG. 2a). In addition, killing of CD8-T11.8-10-17 was also tested with the HLA-A*02 positive NY-ESO-1/LAGE-1 positive tumor cell line MM415 (FIG. 2b). As a negative control, untransduced CD8$^+$ enriched PBMC were used as effector cells (CD8 UT) or the HLA-A*02 positive but NY-ESO-1/LAGE-1 negative tumor cell line SK-Me123 was used as target cells. The co-cultures were set-up at an effector-to-target ratio of about 4:1, i.e. 10,000 adherent tumor cells were seeded one day prior to the co-culture and subsequently 40,000 transgenic TCR$^+$ T cells were added. An increase of red fluorescent target cells (Total Integrated Intensity in GCU×µm$^2$/Image) that indicates induction of apoptosis of target cells (Annexin V, red), was measured every four hours over a total time period of 67 hours using live-cell monitoring (IncuCyte® ZOOM).

Results

T11.8-10-17- or benchmark-TCR-transduced CD8$^+$ T cells showed killing of only the NY-ESO-1/LAGE-1 positive and HLA-A2 positive tumor cell line Me1624.38 (FIG. 2a) or MM415 (FIG. 2b) represented by increase of red fluorescence (IncuCyte® Annexin V) starting already after 10 hours. In contrast, in case of tumor cells cultivated without effector cells or in case of the NY-ESO-1/LAGE-1 negative and HLA-A2 positive tumor cell line SK-Me123 cultivated with T11.8-10-17 transduced CD8$^+$ T cells, no increase of red fluorescence was observed denoting no killing of target cells. Untransduced CD8$^+$ T cells showed no lysis of any tumor cell line.

Example 2.3: Recognition of Tumor Cells

Experimental Layout: Stimulation by Tumor Cell Lines

IFN-γ ELISA was used to assess cytokine secretion upon stimulation of T11.8-10-17-transduced T cells (CD8_T11.8-10-17) with a panel of HLA-A*02:01 positive, NY-ESO-1/LAGE-1 positive human tumor cell lines (Me1624.38, FM6, FM3.29, MM415, SAOS2, U266). NY-ESO-1/LAGE-1 expression in the target cells was detected by NanoString nCounter® analysis. As positive control for T11.8-10-17-transduced T cells, T2 cells were loaded with SLL-peptide ($10^{-5}$ M). As negative controls for the effector function, T11.8-10-17-transduced T cells were co-cultured with T2 cells loaded with irrelevant (FTV) peptide ($10^{-5}$M), SK-Me123 (HLA-A2pos, NY-ESO-1/LAGE-1neg) or SKM1 (HLA-A2pos, NY-ESO-1/LAGE-1neg), or untransduced T cells were co-cultured with tumor cells or peptide-loaded T2 cells. Cultivation of target cells without effector cells served as an additional negative control. Target cells were co-cultured with T cells at a ratio of 2:1 using 40,000 T11.8-10-17-transduced T cells and 20,000 target cells. (FIG. 3).

Results

T11.8-10-17 transgenic CD8$^+$ T cells show high amounts of IFN-γ secretion in co-culture with NY-ESO-1/LAGE-1pos, HLA-A*02pos tumor cell lines Me1624.38, FM6, FM3.29, MM415, SAOS2 and U266 or NY-ESO-1/LAGE-$1_{157-165}$-loaded T2 cells. In contrast, no recognition of the HLA-A*02 positive, NY-ESO-1/LAGE-1 negative tumor cell lines SK-Me123 and SKM1 or irrelevant peptide-loaded T2 cells by T11.8-10-17 transgenic CD8$^+$ T cells was detected. Untransduced T cells co-cultured with any target cells or target cells without effector T cells showed no IFN-γ secretion (FIG. 3).

Example 2.4: Recognition of Mismatched Epitopes

Experimental Layout 2.4.1: Recognition of Peptide Loaded Epitopes

IFN-γ secretion of either NY-ESO-1/LAGE-1$_{157-165}$-specific benchmark-(CD8-benchmark-TCR) or T11.8-10-17-TCR-transduced CD8$^+$ (CD8_T11-10-17) T cells were tested for peptide recognition (IFN-γ secretion) with peptide-loaded ($10^{-5}$ M) T2 cells. By in silico Expitope® analysis (Expitope® 2.0; Jaravine et al. BMC Cancer 2017) of all implemented databases and removing the combined score threshold (set to 0), 75 peptides were tested that are at least 56% homologous (up to 4 mismatches) to the SLL-peptide sequence (9mer) and have a lower MHC (IC50) binding score than 20,000 nM. As a negative control, untransduced CD8$^+$ enriched PBMC (CD8_UT) were used as effector cells or TCR-transgenic T cells were stimulated with irrelevant (irr.; FTVSGNILTI) peptide-loaded T2 cells ($10^{-5}$ M). Background IFN-γ secretion of target cells was also tested (targets only). As a positive control T cells were activated by SLL peptide (#10*)-loaded T2 cells ($10^{-5}$ M). Target cells were co-cultured with T cells at a ratio of 1:1 using 20,000 target cells and 20 000 T11.8-10-17- or benchmark-TCR-transduced or untransduced T cells. IFN-γ secretion was measured by standard ELISA in [pg/mL]. Shown are the six recognized peptides (FIG. 4).

TABLE 1

| Cross-recognized peptide | Antigen name | Peptide sequence | MHC binding affinity [IC50] | SEQ ID NO: |
|---|---|---|---|---|
| #3 | TBC1D32 | ICLQWITQC | 10668 | 17 |
| #6 | ITPR3 | SLLFWILIC | 1076 | 18 |
| #11 | NEMP2 | SLLMWMLRL | 25 | 19 |
| #32 | CD53 | NLLFWICGC | 1190 | 20 |
| #34 | TENM3 | SLMYWITIQ | 2172 | 21 |
| #51 | ZNF446 | QLLGWITAH | 9450 | 22 |

Table 1 shows the peptide sequences of six peptides out of 75 tested peptides that were recognized by T11.8-10-17-TCR-transduced CD8$^+$ (CD8_T11-10-17) T cells.

Results

Shown are peptides cross-recognized by T11.8-10-17- and benchmark-TCR-transgenic CD8$^+$ T cells (peptide sequences are summarized in table 1). Transgenic T cells recognized the positive control peptide (SLL, SLL-MWITQC) but not the irrelevant peptide (irr.; FTVSG-NILTI) and therefore proved functionality of the transgenic T cells. In addition, both transgenic T cells cross-recognized peptide #3 and T11.8-10-17-transgenic T cells were also slightly activated by T2 cells loaded with peptide #6, #11, #32, #34 and #51. No recognition of any T2 cells by untransduced T cells was observed. T cells or T2 target cells cultivated separately did not secrete IFN-γ (FIG. 4).

Experimental Layout 2.4.2: Recognition of ivtRNA Mismatched Epitopes

Specific IFN-γ release of CD8$^+$ enriched PBMC expressing the NY-ESO-1/LAGE-1$_{157-165}$-specific TCR T11.8-10-17 (CD8_T11.8-10-17) or the benchmark-TCR (CD8_benchmark-TCR) in co-culture with either peptide-loaded HLA-A*02:01-transgenic K562 cells (K562-A2+irr., K562-A2+SLL) or with target-ivtRNA transfected HLA-A2-transgenic K562 (K562-A2+NY-ESO-1, K562-A2+eGFP) was tested at 16 hours after setting up the co-culture. For this experiment, $3 \times 10^6$ K562 cells in 300 µl RPMI1640 medium were electroporated with 20 µg either NY-ESO-1 or eGFP-ivtRNA (300 Volt and 300 µF; exponential pulse). As positive control, T cells were stimulated with HLA-A*02:01-transgenic K562 cells loaded with either the SLL-peptide ($10^{-5}$M) (K562-A2+SLL) or with 20 µg ivtRNA encoding NY-ESO-1 (K562-A2+NY-ESO-1). As a negative control HLA-A*02:01-transgenic K562 were either loaded with irrelevant peptide ($10^{-5}$M; K562-A2+FTV) or with 20 µg ivtRNA encoding eGFP (K562-A2+eGFP). In addition, HLA-A*02:01 positive K562 cells were transfected with 20 µg ivtRNA encoding eGFP combined with long peptides comprising cross-recognized epitopes and flanking sequences ((K562-A2+#3, K562-A2+#6, K562-A2+#11, K562-A2+#32, K562-A2+#34, K562-A2+#51) by transgenic T cells expressing either the inventive T11.8-10-17 TCR (CD8_T11.8-10-17) or the benchmark-TCR (CD8 benchmark-TCR). Target cells were co-cultured with T cells at a ratio of 2:1 using 40 000 target cells and 20 000 T11.8-10-17- or benchmark-TCR-transduced T cells. IFN-γ secretion was measured by standard ELISA in [pg/mL] (FIG. 5).

Results

T11.8-10-17- and benchmark-TCR-transgenic CD8$^+$ T cells recognized the positive controls, i.e. either SLL peptide-loaded K562-HLA-A*02:01positive cells (K562-A2+SLL) or NY-ESO-1-ivtRNA transfected K562-HLA-A*02:01positive cells (K562-A2+NYESO), but did not recognize irrelevantly loaded K562-HLA-A*02:01positive cells (K562-A2+irr. and K562-A2+eGFP) proving the specificity and functionality of the transgenic T cells. While benchmark-TCR transgenic T cells were still able to recognize peptide #3 when it is intracellularly processed and presented on K562-HLA-A*02:01positive cells, T11.8-10-17 showed no cross-recognition of any internally processed peptide (#3, #6, #11, #32, #34 and #51) any more. This leads to the conclusion that T11.8-10-17-transgenic T cells do not cross-recognize any of the tested peptides if internally processed in comparison to the benchmark TCR.

Example 3: Cytokine Profile

Experimental Layout 3.1: Secretion of IFN-γ, TNF-α and Granzyme B

Specific cytokine release (IFN-γ, TNF-α and Granzyme B measured in [ng/mL]) of CD8$^+$, transgenic TCR enriched PBMC of two different healthy donors (FIG. 6a: Donor 1; FIG. 6b: Donor 2) genetically modified to express the NY-ESO-1/LAGE-1$_{157-165}$-specific TCR T11.8-10-17 (CD8_T11.8-10-17) or benchmark-TCR (CD8_benchmark-TCR) upon stimulation with HLA-A*02:01 positive T2 cells loaded with either $10^{-5}$ M of the NY-ESO-1/LAGE-1$_{157-165}$ (T2(SLL)) peptide or $10^{-5}$ M of an irrelevant peptide derived from NY-ESO-1 (T2(FTV)) was evaluated.

As negative control, T11.8-10-17- or benchmark-transgenic CD8$^+$ T cells were stimulated with HLA-A*02:01 positive FTV-loaded T2 cells (T2(FTV)) or untransduced CD8+ enriched PBMC (CD8_ut) were co-cultured with peptide-loaded T2 cells. Furthermore, T2 cells or T cells were cultured separately.

Target cells and T cells were co-cultured at a ratio of 1:1 using 10 000 target cells and 10 000 T11.8-10-17- or benchmark-TCR-transduced T cells. Secretion of IFN-γ, TNF-α and Granzyme B by either T11.8-10-17- or benchmark-transgenic CD8+ T cells was determined 18 hours after setting up the co-culture by multiplex assay using the Milliplex MAP Kit and analyzed by the MagPix analyzer.

Results

No significant cytokine release is measured for all negative controls. Both transgenic TCRs lead to comparable amounts of IFN-γ, TNF-α and Granzyme B secretion by the respective T cells and show a preferable cytokine profile in terms of effector function.

Experimental Layout 3.2: Secretion of MIP-1α and MIP-1β

Specific chemokine release (MIP-1α and MIP-1β) of CD8+ enriched PBMC (FIG. 7a: Donor 1 or FIG. 7b: Donor 2) expressing the NY-ESO-1/LAGE-1$_{157-165}$-specific TCR T11.8-10-17 (CD8_T11.8-10-17) or benchmark-TCR (CD8_benchmark-TCR) upon stimulation with HLA-A*02:01 positive T2 cells loaded with either $10^{-5}$M of the NY-ESO-1/LAGE-1$_{157-165}$(SLL) peptide (T2(SLL)) or $10^{-5}$M of an irrelevant peptide derived from NY-ESO-1 (FTV) (T2(FTV)). The benchmark-TCR transgenic T cells secreted higher amounts of MIP-1α and MIP-1β compared to TCR T11.8-10-17 transgenic T cells upon stimulation with SLL peptide-loaded T2 cells.

As negative control, T11.8-10-17- or benchmark-transgenic CD8+ T cells were stimulated with HLA-A*02:01 positive FTV-loaded T2 cells or untransduced CD8+ enriched PBMC (CD8_ut) were co-cultured with peptide-loaded T2 cells. Furthermore, T2 cells or T cells were cultured separately.

Target cells and T cells were co-cultured at a ratio of 1:1 using 10 000 target cells and 10 000 T11.8-10-17- or benchmark-TCR-transduced T cells. Secretion of MIP-1α and MIP-1β by either T11.8-10-17- or benchmark-transgenic CD8+ T cells was determined 18 hours after setting up the co-culture by multiplex assay using the Milliplex MAP Kit and analyzed by the MagPix analyzer.

Results

Negligible chemokine release is measured for all negative controls. Furthermore, T2 cells or T cells cultured separately do not show any chemokine release. T11.8-10-17 transduced T cells released markedly lower amounts of MIP-1α and MIP-1β compared to benchmark-TCR transgenic T cells. As chemokines such as MIP-1α and MIP-1β, also named CCL3 and CLC4 respectively, in particular MIP-1α, are known to promote tumor progression (Liao et al. Oncotarget, 7(4): 4310-4325 (2015); Silva et al. Oncotarget 8 (11): 51024-51036 (2017), Yu Wu et al. J Immunol., November 1; 181(9):6384-93 (2008)), lower MIP-1α and MIP-1β secretion levels are advantageous.

The invention claimed is:

1. A nucleic acid encoding a T cell receptor (TCR), wherein the TCR comprises:
   (a) a TCR α chain comprising a CDR 1 having the amino acid sequence of SEQ ID NO: 4, a CDR 2 having the amino acid sequence of SEQ ID NO: 5, and a CDR 3 having the sequence of SEQ ID NO: 6; and
   (b) a TCR β chain comprising a CDR 1 having the amino acid sequence of SEQ ID NO: 7, a CDR 2 having the amino acid sequence of SEQ ID NO: 8, and a CDR 3 having the sequence of SEQ ID NO: 9.

2. The nucleic acid according to claim 1, wherein the TCR comprises a variable TCR α region having an amino acid sequence which is at least 80% identical to SEQ ID NO: 10 and a variable TCR β region having an amino acid sequence which is at least 80% identical to SEQ ID NO: 11.

3. The nucleic acid according to claim 1, wherein the TCR comprises a variable TCR α region having the amino acid sequence of SEQ ID NO: 10 and a variable TCR β region having the amino acid sequence of SEQ ID NO: 11.

4. The nucleic acid according to claim 1, wherein the TCR comprises a TCR α chain having an amino acid sequence which is at least 80% identical to SEQ ID NO: 12 and a TCR β chain having an amino acid sequence which is at least 80% identical to SEQ ID NO: 13.

5. The nucleic acid according to claim 1, wherein the TCR comprises a TCR α chain having the amino acid sequence of SEQ ID NO: 12 and a TCR β chain having the amino acid sequence of SEQ ID NO: 13.

6. The nucleic acid according to claim 1, wherein the amino acid sequence of the TCR comprises one or more phenotypically silent substitutions.

7. The nucleic acid according to claim 1, wherein the nucleic acid encoding the TCR is modified.

8. The nucleic acid according to claim 1, wherein the TCR is soluble or membrane bound.

9. The nucleic acid according to claim 1, wherein the nucleic acid encoding the TCR is codon optimized.

10. The nucleic acid according to claim 1, wherein the TCR α chain or the TCR β chain is modified to comprise an epitope tag.

11. A vector comprising the nucleic acid of claim 1.

12. The vector according to claim 11, wherein the vector is an expression vector.

13. The vector according to claim 11, wherein the vector is a retroviral vector.

14. The vector according to claim 11, wherein the vector is a lentiviral vector.

15. A cell comprising the vector according to claim 11.

16. A cell comprising the nucleic acid according to claim 1.

17. A pharmaceutical composition comprising the nucleic acid according to claim 1.

18. A method for treating cancer in a human or non-human animal in need thereof, comprising administering to said human or non-human animal the nucleic acid according to claim 1.

19. The method of claim 18, wherein the cancer is a hematological cancer or a solid tumor.

20. The method of claim 18, wherein the cancer is selected from the group consisting of sarcoma, prostate cancer, uterine cancer, thyroid cancer, testicular cancer, renal cancer, pancreatic cancer, ovarian cancer, esophageal cancer, non-small-cell lung cancer, non-Hodgkin's lymphoma, multiple myeloma, melanoma, hepatocellular carcinoma, head and neck cancer, gastric cancer, endometrial cancer, colorectal cancer, cholangiocarcinoma, breast cancer, bladder cancer, myeloid leukemia and acute lymphoblastic leukemia.

* * * * *